(12) United States Patent
Conner et al.

(10) Patent No.: US 7,838,652 B2
(45) Date of Patent: *Nov. 23, 2010

(54) CHIMERIC PROMOTERS COMPRISING A RICE ACTIN 1 PROMOTER AND ENHANCER ELEMENTS FOR USE IN PLANTS

(75) Inventors: Timothy W. Conner, Chesterfield, MO (US); Stanislaw Flasinski, Chesterfield, MO (US); Sheng Z. Pang, Chesterfield, MO (US); Jinsong You, Manchester, MO (US)

(73) Assignee: Monsanto Technology LLC, St. Louis, MO (US)

( * ) Notice: Subject to any disclaimer, the term of this patent is extended or adjusted under 35 U.S.C. 154(b) by 53 days.

This patent is subject to a terminal disclaimer.

(21) Appl. No.: 12/023,350

(22) Filed: Jan. 31, 2008

(65) Prior Publication Data

US 2008/0242547 A1 Oct. 2, 2008

Related U.S. Application Data

(63) Continuation of application No. 11/038,981, filed on Jan. 20, 2005, now Pat. No. 7,371,848.

(60) Provisional application No. 60/537,793, filed on Jan. 20, 2004.

(51) Int. Cl.
*C12N 15/82* (2006.01)
*C07H 21/04* (2006.01)
*A01H 5/00* (2006.01)

(52) U.S. Cl. ............... 536/24.1; 536/23.1; 800/288; 800/295; 800/298; 800/300; 435/320.1; 435/419; 435/468

(58) Field of Classification Search ............... None
See application file for complete search history.

(56) References Cited

U.S. PATENT DOCUMENTS

| | | | |
|---|---|---|---|
| 5,097,025 A | 3/1992 | Benfey et al. | 536/23.6 |
| 5,362,865 A | 11/1994 | Austin | 536/24.1 |
| 5,530,196 A | 6/1996 | Fraley et al. | 800/298 |
| 5,641,876 A | 6/1997 | McElroy et al. | 536/24.1 |
| 6,051,753 A | 4/2000 | Comai et al. | 800/278 |
| 6,429,357 B1 | 8/2002 | McElroy et al. | 800/278 |
| 6,462,258 B1 | 10/2002 | Fincher et al. | 800/300 |
| 6,569,122 B2 | 5/2003 | Fischer et al. | 604/181 |
| 6,670,467 B2 | 12/2003 | Barbour et al. | 536/24.1 |
| 7,371,848 B2 * | 5/2008 | Conner et al. | 536/24.1 |
| 2002/0144304 A1 * | 10/2002 | Fincher et al. | 800/278 |
| 2003/0199681 A1 | 10/2003 | Fincher et al. | 800/300 |
| 2006/0156435 A1 | 7/2006 | Ursin et al. | 800/281 |

FOREIGN PATENT DOCUMENTS

| | | | |
|---|---|---|---|
| WO | WO 00/11185 | * | 3/2000 |
| WO | WO 01/44457 | | 6/2001 |

OTHER PUBLICATIONS

International Search Report for Application No. PCT/US05/02169 dated Jul. 13, 2007.
Kay et al., Duplication of CaMV 35S promoter sequences created a strong enhancer for plant genes, *Science*, 236:1299-1302, 1987.
Benfey et al., "Tissue-specific expression from CaMV 35S enhancer subdomains in early stages of plant development," *EMBO J.*, 9(6):1677-1684, 1990.
Lam et al., "Site-specific mutations alter in vitro factor binding and change promoter expression pattern in transgenic plants," *Proc. Natl. Acad. Sci. USA*, 86:7890-7894, 1989.
Omirulleh et al., "Activity of a chimeric promoter with the double CaMV 35S enhancer element in protoplast-derived cells and transgenic plants in maize," *Plant Molecular Biology*, 21:415-428, 1993.
Supplemental European Search Report for Application No. 07522509.6-2405, dated Jun. 5, 2008.

* cited by examiner

*Primary Examiner*—Cathy Kingdon Worley
(74) *Attorney, Agent, or Firm*—Erin C. Robert, Esq.; Sonnenschein Nath & Rosenthal LLP

(57) ABSTRACT

The present invention provides polynucleotide molecules comprising a rice actin 1 promoter and a promoter enhancer useful for expressing transgenes in plants. The present invention also provides expression constructs containing the polynucleotide molecules useful for expressing transgenes in plants. The present invention also provides transgenic plants and seeds containing the polynucleotide molecules useful for expressing transgenes in plants.

22 Claims, 3 Drawing Sheets

CHIMERIC PROMOTERS COMPRISING A RICE ACTIN 1 PROMOTER AND ENHANCER ELEMENTS FOR USE IN PLANTS

This application is a continuation of U.S. Application No. 11/038,981, filed Jan. 20, 2005, now U.S. Pat. No. 7,371,848, which claims the benefit of U.S. application Ser. No. 60/537,793 filed Jan. 20, 2004, each of the disclosures of which are incorporated herein by reference in their entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01117.rpt, which is 61,440 bytes (measured in MS-DOS) and was created on Jan. 18, 2005 all of which are incorporated herein by reference.

FIELD OF THE INVENTION

The invention relates to the field of plant molecular biology and plant genetic engineering and polynucleotide molecules useful for modulating gene expression in plants.

BACKGROUND

One of the goals of plant genetic engineering is to produce plants with agronomically desirable characteristics or traits. The proper expression of a desirable transgene in a transgenic plant is one way to achieve this goal. Promoters are non-coding polynucleotide molecules which play an integral role in the overall expression of genes in living cells. Isolated promoters that function in plants are useful for modifying plant phenotypes through the methods of genetic engineering.

Many constitutive promoters are available and are useful for providing good overall gene expression. For example, constitutive promoters such as P-FMV, the promoter from the 35S transcript of the Figwort mosaic virus, (U.S. Pat. No. 6,051,753); P-CaMV 35S, the promoter from the 35S RNA transcript of the Cauliflower mosaic virus, (U.S. Pat. No. 5,530,196); P-Rice Actin 1, the promoter from the actin 1 gene of *Oryza sativa*, (U.S. Pat. No. 5,641,876); and P-NOS, the promoter from the nopaline synthase gene of *Agrobacterium tumefaciens* are known to provide some level of gene expression in most or all of the tissues of a plant during most or all of the plant's lifespan. Alternately, many promoters are available with more specific expression patterns such as tissue specificity, temporal specificity, or developmental specificity. These promoters are useful for the targeted expression of a transgene in plants.

Optimal expression of a transgene is useful for producing plants with agronomically desirable characteristics or traits. Such optimal expression often requires a promoter having a specific expression pattern which may not be readily available in known promoters. One example of such a specific expression pattern is a high level of transgene expression in both vegetative and reproductive tissues. The present invention solves this problem by producing novel chimeric promoters containing elements from known promoters. These novel chimeric promoters can then be tested in plants to determine whether the desired expression pattern is indeed achieved.

SUMMARY

In one embodiment the invention provides novel chimeric promoters provided as SEQ ID NO: 9-35 comprising a caulimovirus promoter enhancer fused with a plant actin gene promoter and useful for modulating gene expression in plants. In another embodiment the invention provides constructs comprising the novel chimeric promoter and useful for modulating gene expression in plants. In another embodiment the invention provides a transgenic plant comprising the novel chimeric promoter and the seed of the transgenic plant. In another embodiment the invention provides a method of inhibiting weed growth in a field of transgenic glyphosate tolerant crop plants comprising planting the transgenic plants transformed with an expression cassette comprising the novel chimeric promoter operably linked to a DNA molecule encoding a glyphosate tolerance gene and applying glyphosate to the field at an application rate that inhibits the growth of weeds.

DETAILED DESCRIPTION

Figure 1:
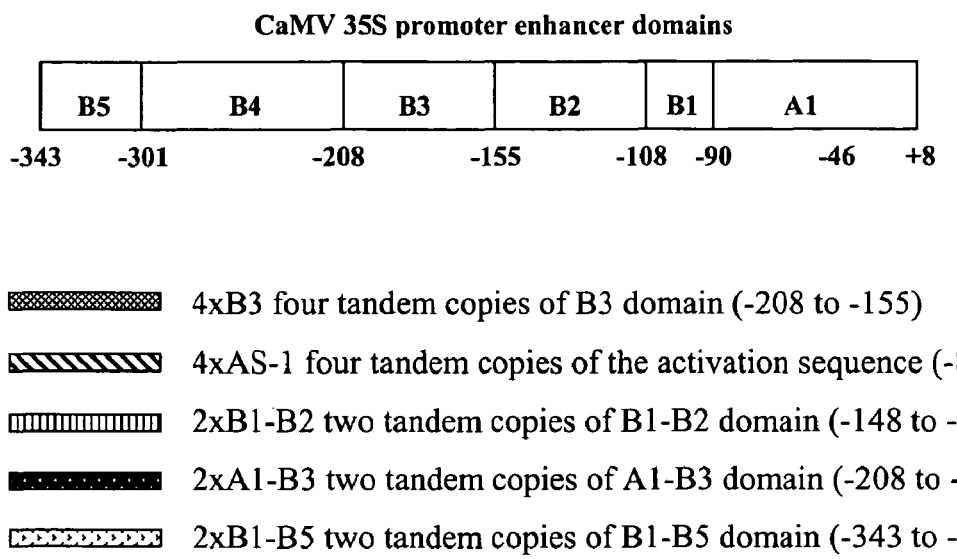
FIG. 1 represents a section of the CaMV 35S promoter with enhancer domains marked. Also diagrammatically represented are five enhancer domains constructed for use in creating chimeric actin promoters.

The following definitions and methods are provided to better define the present invention and to guide those of ordinary skill in the art in the practice of the present invention. Unless otherwise noted, terms are to be understood according to conventional usage by those of ordinary skill in the relevant art.

The invention disclosed herein provides novel combinations of polynucleotide molecules for use in constructing novel chimeric promoters. The design, construction, and use of chimeric or hybrid promoters comprising one or more of the enhancer domains of a caulimovirus 35S promoter and a plant actin gene promoter is one object of this invention. The novel chimeric promoter sequences thereof of SEQ ID NO: 9-35, are capable of transcribing operably linked DNA sequences in multiple tissues and therefore can selectively regulate expression of transgenes in multiple tissues.

As used herein, the term "polynucleotide molecule" refers to the single- or double-stranded DNA or RNA of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for DNA bases as set forth at 37 CFR §1.822 is used.

As used herein, the term "gene regulatory activity" refers to the ability to affect transcription or translation of an operably linked transcribable polynucleotide molecule. An isolated polynucleotide molecule having gene regulatory activity may provide temporal or spatial expression or modulate levels and rates of expression of the operably linked transcribable polynucleotide molecule. An isolated polynucleotide molecule having gene regulatory activity may comprise a promoter, intron, leader, or 3' transcription termination region.

As used herein, the term "gene expression" refers to the transcription of a DNA molecule into a transcribed RNA molecule. Gene expression may be described as related to temporal, spatial, developmental, or morphological qualities as well as quantitative or qualitative indications.

As used herein, the term "regulatory element" refers to a polynucleotide molecule that may affect the transcription or translation of an operably linked transcribable polynucleotide molecule. Regulatory elements such as promoters, leaders, introns, and transcription termination regions are non-coding polynucleotide molecules having gene regulatory activity which play an integral part in the overall expression of genes in living cells. Isolated regulatory elements that function in plants are therefore useful for modifying plant phenotypes through the methods of genetic engineering.

As used herein, the term "promoter" refers to a polynucleotide molecule that is involved in recognition and binding of RNA polymerase II and other proteins (trans-acting transcription factors) to initiate transcription. A plant promoter is a native or non-native promoter that is functional in plant cells. A promoter can be used as a 5' regulatory element for modulating expression of an operably linked transcribable polynucleotide molecule. Promoters may be defined by their temporal, spatial, or developmental expression pattern.

As used herein, the term "enhancer domain" refers to a cis-acting transcriptional regulatory element, a.k.a. cis-element, which confers an aspect of the overall control of gene expression. An enhancer domain may function to bind transcription factors, trans-acting protein factors that regulate transcription. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation. Thus, the design, construction, and use of enhancer domains according to the methods disclosed herein for modulating the expression of operably linked transcribable polynucleotide molecules are encompassed by the present invention As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters, for example, by fusing a heterologous enhancer domain from a first promoter to a second promoter with its own partial or complete regulatory elements. The novel chimeric promoters of the present invention desirably contain at least one enhancer domain fused to a plant actin promoter. Thus, the design, construction, and use of chimeric promoters according to the methods disclosed herein for modulating the expression of operably linked transcribable polynucleotide molecules are encompassed by the present invention.

As used herein, the term "percent sequence identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., Burlington, Mass.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 80% sequence identity, at least about 90% sequence identity, or even greater sequence identity, such as about 98% or about 99% sequence identity. Thus, one embodiment of the invention is a polynucleotide molecule that has at least about 80% sequence identity, at least about 90% sequence identity, or even greater sequence identity, such as about 98% or about 99% sequence identity with a polynucleotide sequence described herein. Polynucleotide molecules that are capable of regulating transcription of operably linked transcribable polynucleotide molecules and have a substantial percent sequence identity to the polynucleotide sequences of the promoters provided herein are encompassed within the scope of this invention.

Promoter Isolation and Modification Methods

Any number of methods well known to those skilled in the art can be used to isolate fragments of a promoter disclosed herein. For example, PCR (polymerase chain reaction) technology can be used to amplify flanking regions from a genomic library of a plant using publicly available sequence information. A number of methods are known to those of skill in the art to amplify unknown polynucleotide molecules adjacent to a core region of known polynucleotide sequence. Methods include but are not limited to inverse PCR (IPCR), vectorette PCR, Y-shaped PCR, and genome walking approaches. Polynucleotide fragments can also be obtained by other techniques such as by directly synthesizing the fragment by chemical means, as is commonly practiced by using an automated oligonucleotide synthesizer. For the present invention, the polynucleotide molecules were isolated by designing PCR primers based on available sequence information.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. The location of the enhancer domain fusion relative to the second promoter may cause the resultant chimeric promoter to have novel expression properties relative to a fusion made at a different location.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Constructs

As used herein, the term "construct" refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more transcribable polynucleotide molecule has been operably linked.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may be part of a single contiguous polynucleotide molecule and may be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule. Methods are known for introducing constructs into a cell in such a manner that the transcribable polynucleotide molecule is transcribed into a functional mRNA molecule that is translated and therefore expressed as a protein product. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, *Molecular Cloning: A Laboratory Manual, 3rd edition Volumes 1, 2, and 3* (2000). J. F. Sambrook, D. W. Russell, and N. Irwin, Cold Spring Harbor Laboratory Press.

Constructs of the present invention would typically contain a promoter operably linked to a transcribable polynucleotide molecule operably linked to a 3' transcription termination polynucleotide molecule. In addition, constructs may include but are not limited to additional regulatory polynucleotide molecules from the 3'-untranslated region (3' UTR) of plant genes (e.g., a 3' UTR to increase mRNA stability of the mRNA, such as the PI-II termination region of potato or the octopine or nopaline synthase 3' termination regions). Constructs may include but are not limited to the 5' untranslated regions (5' UTR) of an mRNA polynucleotide molecule which can play an important role in translation initiation and can also be a genetic component in a plant expression construct. For example, non-translated 5' leader polynucleotide molecules derived from heat shock protein genes have been demonstrated to enhance gene expression in plants (see for example, U.S. Pat. No. 5,659,122 and U.S. Pat. No. 5,362,865, all of which are incorporated herein by reference). These additional upstream and downstream regulatory polynucleotide molecules may be derived from a source that is native or heterologous with respect to the other elements present on the construct.

Thus, one embodiment of the invention is a promoter such as provided in SEQ ID NO: 9-35, operably linked to a transcribable polynucleotide molecule so as to direct transcription of said transcribable polynucleotide molecule at a desired level or in a desired tissue or developmental pattern upon introduction of said construct into a plant cell. In one embodiment, the transcribable polynucleotide molecule comprises a protein-coding region of a gene, and the promoter provides for transcription of a functional mRNA molecule that is translated and expressed as a protein product. In another embodiment, the transcribable polynucleotide molecule comprises an antisense region of a gene, and the regulatory element affects the transcription of an antisense RNA molecule or other similar inhibitory RNA in order to inhibit expression of a specific RNA molecule of interest in a target host cell.

Exemplary transcribable polynucleotide molecules for incorporation into constructs of the present invention include, for example, polynucleotide molecules or genes from a species other than the target species or genes that originate with or are present in the same species, but are incorporated into recipient cells by genetic engineering methods rather than classical reproduction or breeding techniques. The type of polynucleotide molecule can include but is not limited to a polynucleotide molecule that is already present in the plant cell, a polynucleotide molecule from another plant, a polynucleotide molecule from a different organism, or a polynucleotide molecule generated externally, such as a polynucleotide molecule containing an antisense message of a gene, or a polynucleotide molecule encoding an artificial, synthetic, or otherwise modified version of a transgene.

The regulatory elements of the present invention can be incorporated into a construct using marker genes as described and tested in transient or stable plant analyses to provide an indication of the regulatory element's gene expression pattern in stable transgenic plants. As used herein the term "marker gene" refers to any transcribable polynucleotide molecule whose expression can be screened for or scored in some way. Marker genes for use in the practice of the present invention include, but are not limited to transcribable polynucleotide molecules encoding β-glucuronidase (GUS described in U.S. Pat. No. 5,599,670, which is incorporated herein by reference) and green fluorescent protein (GFP described in U.S. Pat. No. 5,491,084 and U.S. Pat. No. 6,146,826, both of which are incorporated herein by reference), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides. Polynucleotide molecules encoding proteins involved in herbicide tolerance are known in the art, and include, but are not limited to a polynucleotide molecule encoding 5-enolpyruvylshikimate-3-phosphate synthase (EPSPS described in U.S. Pat. No. 5,627,061, U.S. Pat. No. 5,633,435, U.S. Pat. No. 6,040, 497 and in U.S. Pat. No. 5,094,945 for glyphosate tolerance, all of which are incorporated herein by reference); polynucleotides encoding a glyphosate oxidoreductase and a glyphosate-N-acetyl transferase (GOX described in U.S. Pat. No. 5,463,175 and GAT described in U.S. Patent publication 20030083480, both of which are incorporated herein by reference); a polynucleotide molecule encoding bromoxynil nitrilase (Bxn described in U.S. Pat. No. 4,810,648 for Bromoxynil tolerance, which is incorporated herein by reference); a polynucleotide molecule encoding phytoene desaturase (crtI) described in Misawa et al, (1993) *Plant J.* 4:833-840 and Misawa et al, (1994) *Plant J.* 6:481-489 for norflurazon tolerance: a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; a polynucleotide molecule encoding a dicamba-degrading oxygenase enzyme (described in U.S. Patent Publications US20030135879 and US20030115626, for dicamba tolerance, all of which are incorporated herein by reference); and the bar gene described in DeBlock, et al. (1987) *EMBO J.* 6:2513-2519 for glufosinate and bialaphos tolerance. The regulatory elements of the present invention can express transcribable polynucleotide molecules that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Thus, in one embodiment of the invention, a polynucleotide molecule of the present invention as shown in SEQ ID NO: 9-35 is incorporated into a DNA construct such that a polynucleotide molecule of the present invention is operably linked to a transcribable polynucleotide molecule that provides for a selectable, screenable, or scorable marker. The constructs containing the regulatory elements operably linked to a marker gene may be delivered to the tissues and the tissues analyzed by the appropriate mechanism, depending on the marker. The quantitative or qualitative analyses are used as a tool to evaluate the potential expression profile of a regulatory element when operatively linked to a gene of agronomic interest in stable plants. Any marker gene can be used in a transient assay. Methods of testing for marker gene expression in transient assays are known to those of skill in the art. Transient expression of marker genes has been reported using a variety of plants, tissues, and DNA delivery systems. For example, types of transient analyses can include but are not limited to direct gene delivery via electroporation or particle bombardment of tissues in any transient plant assay using any plant species of interest. Such transient systems would include but are not limited to electroporation of protoplasts from a variety of tissue sources or particle bombardment of specific tissues of interest. The present invention encompasses the use of any transient expression system to evaluate regulatory elements operably linked to any transcribable polynucleotide molecule, including but not limited to marker genes or genes of agronomic interest. Examples of plant tissues envisioned to test in transients via an appropriate delivery system would include but are not limited to leaf base tissues, callus, cotyledons, roots, endosperm, embryos, floral tissue, pollen, and epidermal tissue.

In one embodiment of the invention, a polynucleotide molecule as shown in SEQ ID NO: 9-35 is incorporated into a construct such that a polynucleotide molecule of the present invention is operably linked to a transcribable polynucleotide molecule that is a gene of agronomic interest. As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance. The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 6,803,501; 6,448,476; 6,248,876; 6,225,114; 6,107,549; 5,866,775; 5,804,425; 5,633,435; 5,463,175; and U.S. Patent Publications US20030135879 and US20030115626), increased yield (U.S. Pat. Nos. USRE38,446; 6,716,474; 6,663,906; 6,476,295; 6,441,277; 6,423,828; 6,399,330; 6,372,211; 6,235,971; 6,222,098; 5,716,837), insect control (U.S. Pat. Nos. 6,809,078; 6,713,063; 6,686,452; 6,657,046; 6,645,497; 6,642,030; 6,639,054; 6,620,988; 6,593,293; 6,555,655; 6,538,109; 6,537,756; 6,521,442; 6,501,009; 6,468,523; 6,326,351; 6,313,378; 6,284,949; 6,281,016; 6,248,536; 6,242,241; 6,221,649; 6,177,615; 6,156,573; 6,153,814; 6,110,464; 6,093,695; 6,063,756; 6,063,597; 6,023,013; 5,959,091; 5,942,664; 5,942,658, 5,880,275; 5,763,245; 5,763,241), fungal disease resistance (U.S. Pat. Nos. 6,653, 280; 6,573,361; 6,506,962; 6,316,407; 6,215,048; 5,516,671; 5,773,696; 6,121,436; 6,316,407; 6,506,962), virus resistance (U.S. Pat. Nos. 6,617,496; 6,608,241; 6,015,940; 6,013, 864; 5,850,023; 5,304,730), nematode resistance (U.S. Pat. No. 6,228,992), bacterial disease resistance (U.S. Pat. No. 5,516,671), plant growth and development (U.S. Pat. Nos. 6,723,897; 6,518,488), starch production (U.S. Pat. Nos. 6,538,181; 6,538,179; 6,538,178; 5,750,876; 6,476,295), modified oils production (U.S. Pat. Nos. 6,444,876; 6,426, 447; 6,380,462), high oil production (U.S. Pat. Nos. 6,495, 739; 5,608,149; 6,483,008; 6,476,295), modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018), high protein production (U.S. Pat. No. 6,380,466), fruit ripening (U.S. Pat. No. 5,512,466), enhanced animal and human nutrition (U.S. Pat. Nos. 6,723, 837; 6,653,530; 6,5412,59; 5,985,605; 6,171,640), biopolymers (U.S. Pat. Nos. USRE37,543; 6,228,623; 5,958,745 and U.S. Patent Publication No. US20030028917), environmental stress resistance (U.S. Pat. No. 6,072,103), pharmaceutical peptides and secretable peptides (U.S. Pat. Nos. 6,812,379; 6,774,283; 6,140,075; 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), fiber production (U.S. Pat. Nos. 6,576,818; 6,271,443; 5,981,834; 5,869,720) and biofuel production (U.S. Pat. No. 5,998,700); the genetic elements, methods, and transgenes described in the patents listed above are incorporated herein by reference.

Alternatively, a transcribable polynucleotide molecule can effect the above mentioned plant characteristic or phenotypes by encoding a RNA molecule that causes the targeted inhibition of expression of an endogenous gene, for example via antisense, inhibitory RNA (RNAi), or cosuppression-mediated mechanisms. The RNA could also be a catalytic RNA molecule (i.e., a ribozyme) engineered to cleave a desired endogenous mRNA product. Thus, any transcribable polynucleotide molecule that encodes a transcribed RNA molecule that affects a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, which along with transfer molecules provided by the *Agrobacterium* cells, permit the integration of the T-DNA into the genome of a plant cell. The constructs may also contain the plasmid backbone DNA segments that provide replication function and antibiotic selection in bacterial cells, for example, an *Escherichia coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants and Plant Cells

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule. A plant transformation construct containing a promoter of the present invention may be introduced into plants by any plant transformation method. Methods and materials for transforming plants by introducing a plant expression construct into a plant genome in the practice of this invention can include any of the well-known and demonstrated methods including electroporation (as illustrated in U.S. Pat. No. 5,384,253; microprojectile bombardment as illustrated in U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,824,877; U.S. Pat. No. 5,591,616; U.S. Pat. No. 5,981, 840; and U.S. Pat. No. 6,384,301; and protoplast transformation as illustrated in U.S. Pat. No. 5,508,184, all of which are incorporated herein by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Still yet another aspect of the invention is a method of inhibiting weed growth in a field of transgenic crop plants comprising first planting the transgenic plants transformed with an expression cassette comprising a polynucleotide sequence selected from the group consisting of SEQ ID NO: 9-35 operably linked to a transcribable polynucleotide molecule encoding a glyphosate tolerance gene and then applying glyphosate to the field at an application rate that inhibits the growth of weeds, wherein the growth and yield of the transgenic crop plant is not substantially affected by the glyphosate application. The glyphosate application rate is the effective rate necessary to control weeds in a particular glyphosate tolerant crop; these rates may range from 8 ounces/acre to 256 ounces/acre, preferably 16 ounces/acre to 128 ounces/acre, and more preferably 32 ounces/acre to 96 ounces/acre. The glyphosate is applied at least once during the growth of the glyphosate tolerant crop and may be applied 2, 3, or 4 times during the growth of the crop or more as necessary to control weeds in the field.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Construction of Chimeric Promoters

Novel chimeric promoters are constructed by fusing at least one enhancer domain from a Caulimovirus promoter with a plant actin gene promoter. A brief description of the sequences referred to herein is provided in Table 1 below.

TABLE 1

Brief Listing of the SEQ ID NO

| SEQ ID NO | Sequence Name | Brief Description |
|---|---|---|
| 1 | P-CaMV.35S | 35S promoter sequence from the Cauliflower mosaic virus |
| 2 | 4xB3 | P-CaMV.35S Enhancer Domain -- four tandem copies of the B3 domain (−208 to −155) as described in U.S. Pat. No. 5,097,025 |
| 3 | 4xAS-1 | P-CaMV.35S Enhancer Domain -- four tandem copies of the "activation sequence" (−83 to −62) as described in U.S. Pat. No. 5,097,025 |
| 4 | 2xB1-B2 | P-CaMV.35S Enhancer Domain -- two tandem copies of the B1-B2 domain (−148 to −90) as described in U.S. Pat. No. 5,097,025 |
| 5 | 2xA1-B3 | P-CaMV.35S Enhancer Domain -- two tandem copies of the A1-B3 domain (−208 to −46) as described in U.S. Pat. No. 5,097,025 |
| 6 | 2xB1-B5 | P-CaMV.35S Enhancer Domain -- two tandem copies of the B1-B5 domain (−343 to −90) as described in U.S. Pat. No. 5,097,025 |
| 7 | P-Os.Act1 | Rice actin 1 promoter |
| 8 | P-At.Act1 | *Arabidopsis* Actin 1 promoter |
| 9 | P-4xB3/P-Os.Act1-1 | Chimeric promoter -- 4xB3 fused to the rice Act1 promoter at the −848 nt position |
| 10 | P-4xB3/P-Os.Act1-2 | Chimeric promoter -- 4xB3 fused to the rice Act1 promoter at the −462 nt position |
| 11 | P-4xB3/P-Os.Act1-3 | Chimeric promoter -- 4xB3 fused to the rice Act1 promoter at the −80 nt position |
| 12 | P-4xAS-1/P-Os.Act1-1 | Chimeric promoter -- 4xAS-1 fused to the rice Act1 promoter at the −848 nt position |
| 13 | P-4xAS-1/P-Os.Act1-2 | Chimeric promoter -- 4xAS-1 fused to the rice Act1 promoter at the −462 nt position |
| 14 | P-4xAS-1/P-Os.Act1-3 | Chimeric promoter -- 4xAS-1 fused to the rice Act1 promoter at the −80 nt position |
| 15 | P-2xB1-B2/P-Os.Act1-1 | Chimeric promoter -- 2xB1-B2 fused to the rice Act1 promoter at the −848 nt position |
| 16 | P-2xB1-B2/P-Os.Act1-2 | Chimeric promoter -- 2xB1-B2 fused to the rice Act1 promoter at the −462 nt position |
| 17 | P-2xB1-B2/P-Os.Act1-3 | Chimeric promoter -- 2xB1-B2 fused to the rice Act1 promoter at the −80 nt position |
| 18 | P-2xA1-B3/P-Os.Act1-1 | Chimeric promoter -- 2xA1-B3 fused to the rice Act1 promoter at the −848 nt position |
| 19 | P-2xA1-B3/P-Os.Act1-2 | Chimeric promoter -- 2xA1-B3 fused to the rice Act1 promoter at the −462 nt position |
| 20 | P-2xA1-B3/P-Os.Act1-3 | Chimeric promoter -- 2xA1-B3 fused to the rice Act1 promoter at the −80 nt position |
| 21 | P-2xB1-B5/P-Os.Act1-1 | Chimeric promoter -- 2xB1-B5 fused to the rice Act1 promoter at the −848 nt position |
| 22 | P-2xB1-B5/P-Os.Act1-2 | Chimeric promoter -- 2xB1-B5 fused to the rice Act1 promoter at the −462 nt position |
| 23 | P-2xB1-B5/P-Os.Act1-3 | Chimeric promoter -- 2xB1-B5 fused to the rice Act1 promoter at the −80 nt position |
| 24 | P-2xA1-B3/At.Act1/ArvII | Chimeric promoter -- 2xA1-B3 fused to the *Arabidopsis* Act1 promoter at the ArvII position |
| 25 | P-2xA1-B3/At.Act1/BstZI | Chimeric promoter -- 2xA1-B3 fused to the *Arabidopsis* Act1 promoter at the BstZI position |
| 26 | P-2xA1-B3/At.Act1/BstZI-R | Chimeric promoter -- 2xA1-B3 fused to the *Arabidopsis* Act1 promoter at the BstZI position in reverse orientation |
| 27 | P-2xA1-B3/At.Act1/NsiI | Chimeric promoter -- 2xA1-B3 fused to the *Arabidopsis* Act1 promoter at the NsiI position |
| 28 | P-2xA1-B3/At.Act1/NsiI-R | Chimeric promoter -- 2xA1-B3 fused to the *Arabidopsis* Act1 promoter at the NsiI position in reverse orientation |
| 29 | P-2xA1-B3/At.Act1/BsmFI | Chimeric promoter -- 2xA1-B3 fused to the *Arabidopsis* Act1 promoter at the BsmFI position |
| 30 | P-4xAS-1/At.Act1/ArvII | Chimeric promoter -- 4xAS-1 fused to the *Arabidopsis* Act1 promoter at the ArvII position |
| 31 | P-4xAS-1/At.Act1/ArvII-R | Chimeric promoter -- 4xAS-1 fused to the *Arabidopsis* Act1 promoter at the ArvII position in reverse orientation |
| 32 | P-4xAS-1/At.Act1/BstZI | Chimeric promoter -- 4xAS-1 fused to the *Arabidopsis* Act1 promoter at the BstZi position |
| 33 | P-4xAS-1/At.Act1/BstZI-R | Chimeric promoter -- 4xAS-1 fused to the *Arabidopsis* Act1 promoter at the BstZI position in reverse orientation |
| 34 | P-4xAS-1/At.Act1/NsiI | Chimeric promoter -- 4xAS-1 fused to the *Arabidopsis* Act1 promoter at the NsiI position |
| 35 | P-4xAS-1/At.Act1/BsmFI | Chimeric promoter -- 4xAS-1 fused to the *Arabidopsis* Act1 promoter at the BsmFI position |

The Caulimovirus promoter can be any promoter from a virus in the Caulimovirus family, including but not limited to promoters from Cauliflower mosaic virus (CaMV) such as the promoter from the 35S RNA transcript of the Cauliflower mosaic virus (P-CaMV.35S) (SEQ ID NO: 1) (U.S. Pat. No. 5,530,196) and promoters from Figwort mosaic virus (FMV) such as the promoter from the 35S transcript of the Figwort mosaic virus, (U.S. Pat. No. 6,051,753), all of which are incorporated herein by reference. Promoter enhancer domains constructed as multimers of enhancer domains from the P-CaMV.35S promoter include but are not limited to the 4xB3 domain (SEQ ID NO: 2), 4xAS-1 (SEQ ID NO: 3), 2xB1-B2 domain (SEQ ID NO: 4), 2xA1-B3 domain (SEQ ID NO: 5), and 2xB1-B5 domain (SEQ ID NO: 6). See FIG. 1. The monomers comprising the multimers listed above as well as other enhancer domains from P-CaMV.35S are described in U.S. Pat. No. 5,097,025, incorporated herein by reference.

The plant actin gene promoter can be any promoter from a plant actin gene, including but not limited to actin promoters from *Oryza sativa* such as the rice actin 1 promoter (P-Os.Act1) (SEQ ID NO: 7) (U.S. Pat. No. 5,641,876), actin promoters from *Arabidopsis thaliana* such as the *Arabidopsis* Actin 1 promoter (P-At.Act1) (SEQ ID NO: 8), and actin promoters from *Zea mays* such as the Actin-2 promoter (U.S. Pat. No. 6,670,467), all of which are incorporated herein by reference.

The fusion of at least one enhancer domain with a plant actin gene promoter may be to any region of the plant actin gene promoter including but not limited to the 5' end of the plant actin gene promoter, the 3' end of the plant actin gene promoter, or any region internal to the plant actin gene promoter. The enhancer domain may be in either the reverse or the forward orientation.

Figure 2:
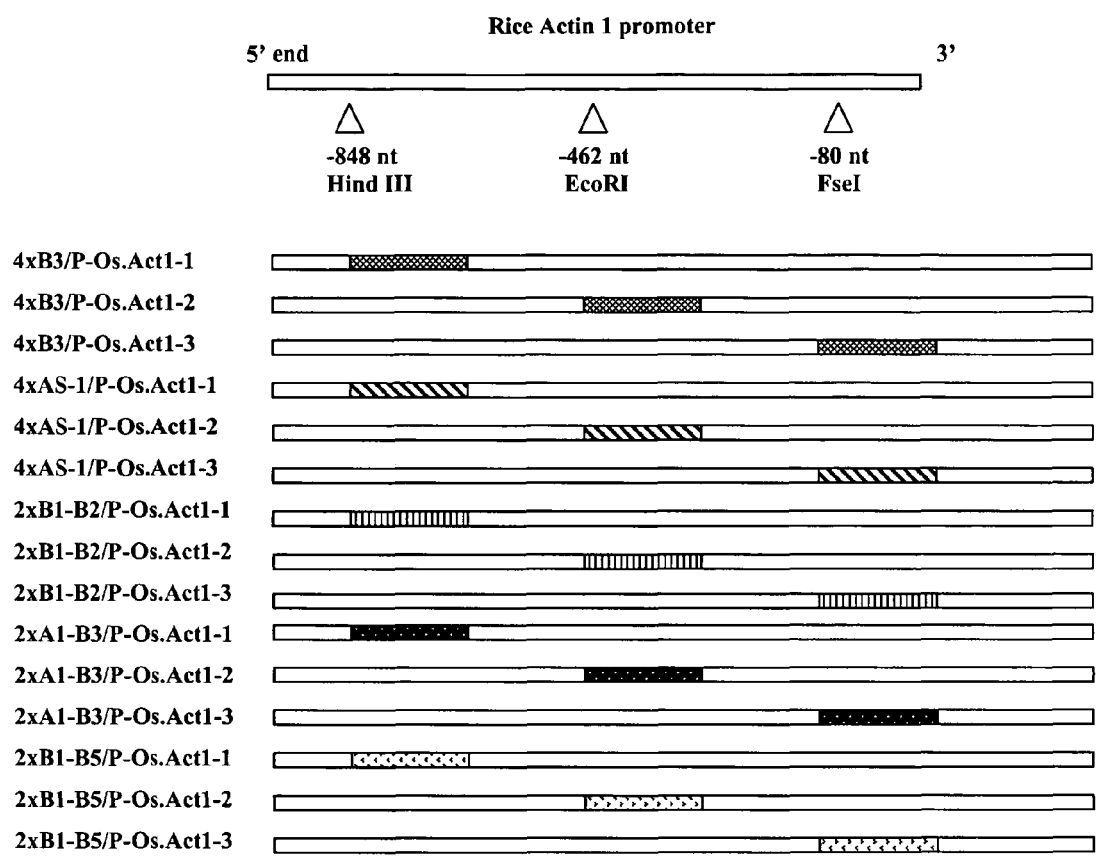
FIG. 2 represents the native rice actin 1 promoter and novel chimeric promoters made by fusing the rice actin 1 promoter and selected CaMV 35S promoter enhancer domains.

Enhancer domains derived from P-CaMV.35S were inserted in three locations in the rice actin 1 (relative to rice Actin1 transcription initiation site): −848 nt (HindIII site), −462 nt (EcoRI site), and −80 nt (FseI site). See FIG. 2. Construction of these chimeric promoters is described in detail below.

The P-4xB3/P-Os.Act1 chimeric promoters were created by fusing the four tandem copies CaMV 35S B3 enhancer sequence to the rice Act1 promoter (P-Os.Act1). Chimeras were made by fusing the enhancer region at the −848 nt position of P-Os.Act1 (SEQ ID NO: 9), at the −462 nt position of P-Os.Act1 (SEQ ID NO: 10) and at the −80 nt position of P-Os.Act1 (SEQ ID NO: 11).

The P-4xAS-1/P-Os.Act1 chimeric promoter was created by fusing four tandem copies of the CaMV 35S AS-1 enhancer sequence to the rice Act1 promoter (P-Os.Act1). Chimeras were made by fusing the enhancer region at the −848 nt position of P-Os.Act1 (SEQ ID NO: 12), at the −462 nt position of P-Os.Act1 (SEQ ID NO: 13) and at the −80 nt position of P-Os.Act1 (SEQ ID NO: 14).

The P-2xB1-B2/P-Os.Act1 chimeric promoter was created by fusing two tandem copies of the CaMV 35S B1-B2 enhancer sequence to the rice Act1 promoter (P-Os.Act1). Chimeras were made by fusing the enhancer region at the −848 nt position of P-Os.Act1 (SEQ ID NO: 15), at the −462 nt position of P-Os.Act1 (SEQ ID NO: 16) and at the −80 nt position of P-Os.Act1 (SEQ ID NO: 17).

The P-2xA1-B3/P-Os.Act1 chimeric promoters were created by fusing two tandem copies of the CaMV 35S A1-B3 enhancer sequence to the rice Act1 promoter (P-Os.Act1). Chimeras were made by fusing the enhancer region at the −848 nt position of P-Os.Act1 (SEQ ID NO: 18), at the −462 nt position of P-Os.Act1 (SEQ ID NO: 19), and at the −80 nt position of P-Os.Act1 (SEQ ID NO: 20).

The P-2xB1-B5/P-Os.Act1 chimeric promoter was created by fusing two tandem copies of the CaMV 35S B1-B5 enhancer sequence to the rice Act1 promoter (P-Os.Act1). Chimeras were made by fusing the enhancer region at the −848 nt position of P-Os.Act1 (SEQ ID NO: 21), at the −462 nt position of P-Os.Act1 (SEQ ID NO: 22) and at the −80 nt position of P-Os.Act1 (SEQ ID NO: 23).

Enhancer domains derived from P-CaMV.35S were inserted in four locations in the *Arabidopsis* actin 1 promoter (P-At.Act1) (with the P-At.Act1 transcription initiation site designated as +1). Four unique restriction sites in P-At.Act1 were used as insertion sites: AvrII, BstZI, NsiI, BsmFI. Construction of these chimeric promoters is described in detail below.

Figure 3:
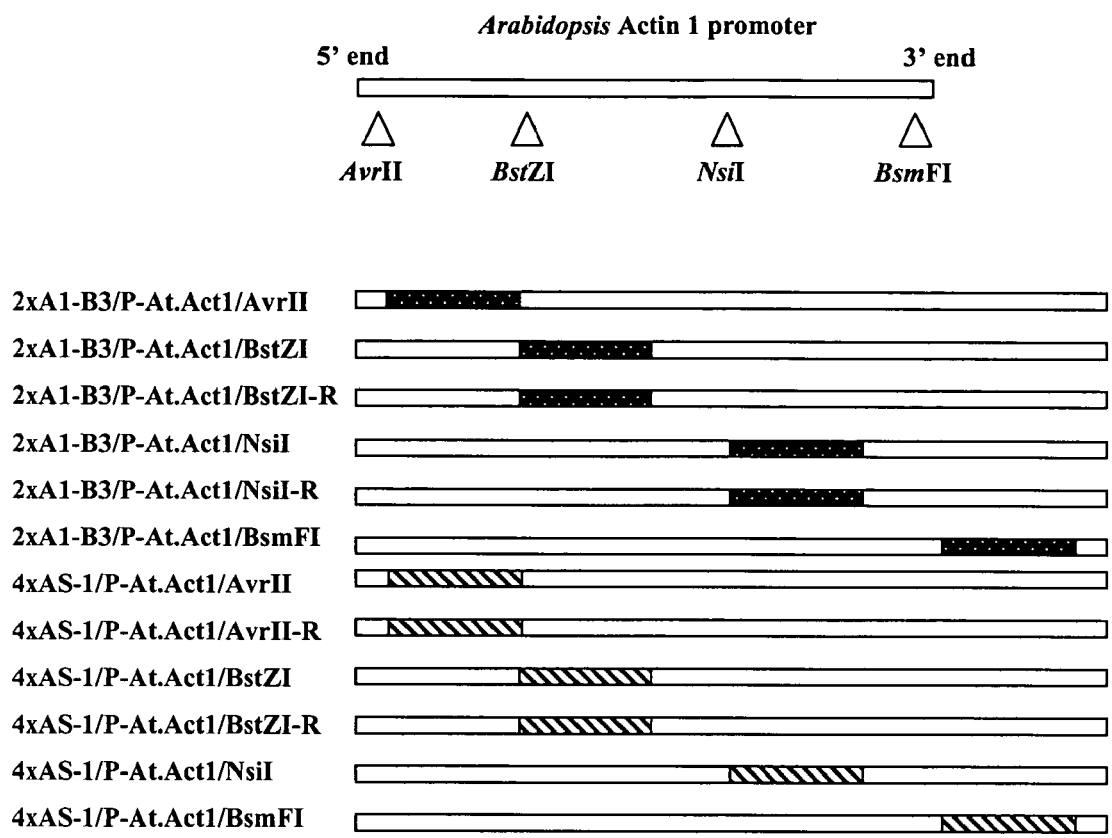
FIG. 3 represents the native *Arabidopsis* actin 1 promoter and novel chimeric promoters made by fusing the *Arabidopsis* actin 1 promoter and selected CaMV 35S promoter enhancer domains.

The 2xA1B3 and 4xAS-1 fragments were isolated by restriction enzyme digest. Fragments ends were then made blunt by treatment with T4 DNA polymerase. Vectors containing the P-At.Act1 promoter were cut with one of the four unique enzymes and then the fragment ends were made blunt. Each of the two enhancer domains was fused into each of the four blunted restriction enzyme sites. Chimeric promoters were selected with inserts in both the reverse and forward orientations. See FIG. 3.

Selected chimeric promoters were subcloned into a binary vector to operably link the chimeric promoter with a reporter gene such as the GUS reporter gene (β-glucuronidase gene) or the CP4 gene (for glyphosate tolerance). These vectors were used for plant transformation and subsequent promoter characterization. Transgene expression levels of the chimeric promoters were compared with the transgene expression levels of control constructs.

Example 2

Promoter Characterization in Transient Systems

Selected chimeric promoters were used for transient transformation for reporter expression analysis. Transient systems used included tobacco protoplasts, corn protoplasts, wheat ovary, wheat anther, and barley microspores. Cells were harvested and protein extracted for GUS activity analysis. Methods for measuring GUS activity are well known to those skilled in the art, see for instance *Using the Gus Gene as a Reporter of Gene Expression* (1992) edited by Sean R. Gallagher, Academic Press, Inc., San Diego.

Monocot Analysis

Constructs containing chimeric P-Os.Act1 promoters were used to transform corn protoplasts and assay for GUS/LUX activity relative to the P-Os.Act1 promoter and the P-CaMV.e35S promoter. Data are provided in Table 2.

TABLE 2

Transient Analysis in Corn Protoplasts

| Chimeric Promoter | SEQ ID NO | Construct | Relative activity |
| --- | --- | --- | --- |
| P-Os.Act1 | 7 | pMON25455 | 1.0 |
| P-2xB1-B5/P-Os.Act1-1 | 21 | pMON38303 | 1.6 |
| P-2xB1-B5/P-Os.Act1-2 | 22 | pMON38304 | 1.1 |
| P-2xB1-B5/P-Os.Act1-3 | 23 | pMON38305 | 3.6 |
| P-2xA1-B3/P-Os.Act1-1 | 18 | pMON38310 | 4.5 |
| P-2xA1-B3/P-Os.Act1-2 | 19 | pMON38312 | 4.6 |
| P-2xA1-B3/P-Os.Act1-3 | 20 | pMON38314 | 11.0 |
| P-2xB1-B2/P-Os.Act1-1 | 15 | pMON38309 | 1.1 |
| P-2xB1-B2/P-Os.Act1-2 | 16 | pMON38311 | 1.5 |

TABLE 2-continued

Transient Analysis in Corn Protoplasts

| Chimeric Promoter | SEQ ID NO | Construct | Relative activity |
|---|---|---|---|
| P-2xB1-B2/P-Os.Act1-3 | 17 | pMON38313 | 2.2 |
| P-4xAS-1/P-Os.Act1-1 | 12 | pMON38300 | 1.8 |
| P-4xAS-1/P-Os.Act1-2 | 13 | pMON38301 | 1.3 | necessarily indicative of performance in reproductive tissue. A few selected chimeric promoters were therefore further tested for GUS activity (pmol/min in 10 ul) in wheat anther, wheat ovary, barley microspore, and corn pollen transient assay systems for comparison with corn leaf protoplast data. Data are provided in Table 3 below. In comparison to P-Os.Act1 promoter which is known to express well in reproductive tissue, these chimeric promoters did not show any decrease of activity in reproductive tissue.

TABLE 3

Transient Analysis of Selected Chimeric Promoters in Reproductive Tissues

| Promoter | SEQ ID NO | Construct | Wheat Anther | Wheat Ovary | Barley Microspore | Corn Pollen |
|---|---|---|---|---|---|---|
| P-Os.Act1 | 7 | pMON25455 | 1.0 | 1.0 | 1.0 | 1.0 |
| P-CaMV.E35S | 1 | pMON25456 | 3.3 | 0.5 | 0.8 | 0.03 |
| P-4xAS-1/P-Os.Act1-3 | 14 | pMON38302 | 16.4 | 1.2 | 2.0 | 2.2 |
| P-4xB3/P-Os.Act1-2 | 10 | pMON38307 | 1.5 | 2.1 | — | 6.0 |
| P-4xB3/P-Os.Act1-3 | 11 | pMON38308 | 6.4 | 2.5 | — | 0.6 |
| P-2xA1-B3/P-Os.Act1-1 | 18 | pMON38310 | 3.3 | 1.3 | 2.0 | 1.4 |
| P-2xA1-B3/P-Os.Act1-2 | 19 | pMON38312 | 7.6 | 3.3 | 2.4 | 0.5 |
| P-2xA1-B3/P-Os.Act1-3 | 20 | pMON38314 | 13.2 | 3.9 | 7.8 | 0.05 |

TABLE 2-continued

Transient Analysis in Corn Protoplasts

| Chimeric Promoter | SEQ ID NO | Construct | Relative activity |
|---|---|---|---|
| P-4xAS-1/P-Os.Act1-3 | 14 | pMON38302 | 8.9 |
| P-4xB3/P-Os.Act1-1 | 9 | pMON38306 | 1.8 |
| P-4xB3/P-Os.Act1-2 | 10 | pMON38307 | 3.3 |
| P-4xB3/P-Os.Act1-3 | 11 | pMON38308 | 5.4 |
| P-CaMV.e35S | 1 | pMON25456 | 5.1 |

All the chimeric promoters tested were found to have higher activity than the native P-Os.Act1 promoter when tested in corn protoplasts. The three chimeric promoters P-2xA1-B3/P-Os.Act1-3 (SEQ ID NO: 20), P-4xAS-1/P-Os.Act1-3 (SEQ ID NO: 14), and P-4-xB3/P-Os.Act1-3 (SEQ ID NO: 11) also showed increased activity when compared to the CaMV e35S promoter. Two factors contributed the enhanced activity in the chimeric promoter, namely the enhancer domain selected and the fusion location of the enhancer domain. Every enhancer domain tested appeared to be more powerful when the fusion location was closer to the 3' end of the promoter, and attenuated when the fusion location was at the 5' end of the promoter. Among the enhancer domains tested, the 2xA1-B3 enhancer was found to be the strongest enhancer domain in corn protoplasts. The 4xAS-1 enhancer was found to convey desirable strength to the chimeric promoter. The 4xB3 enhancer was found to be most effective when fused closer to the transcription start site.

One limitation of expression analysis in the corn protoplast system is that it only represents vegetative tissue. An increased expression level in the corn protoplast system is not Dicot Analysis Constructs containing chimeric P-At.Act1 promoters were used to transform tobacco protoplasts and assay for GUS activity (nM MUG/µg total protein). Data are provided in Table 4 below.

TABLE 4

Transient Analysis in Tobacco Protoplasts

| Chimeric Promoter | SEQ ID NO | Construct | GUS Activity |
|---|---|---|---|
| P-At.Act1 | 8 | pMON54945 | 10 |
| P-2xA1-B3/At.Act1/ArvII | 24 | pMON59394 | 18 |
| P-2xA1-B3/At.Act1/BstZI | 25 | pMON59392 | 20 |
| P-2xA1-B3/At.Act1/BstZI-R | 26 | pMON59392-R | 16 |
| P-2xA1-B3/At.Act1/NsiI | 27 | pMON59386 | 23 |
| P-2xA1-B3/At.Act1/NsiI-R | 28 | pMON59386-R | 12 |
| P-2xA1-B3/At.Act1/BsmFI | 29 | pMON59384 | 65 |
| P-4xAS-1/At.Act1/ArvII | 30 | pMON59393 | 19 |
| P-4xAS-1/At.Act1/ArvII-R | 31 | pMON59393-R | 15 |
| P-4xAS-1/At.Act1/BstZI | 32 | pMON59391 | 16 |
| P-4xAS-1/At.Act1/BstZI-R | 33 | pMON59391-R | 21 |
| P-4xAS-1/At.Act1/NsiI | 34 | pMON59385 | 150 |
| P-4xAS-1/At.Act1/BsmFI | 35 | pMON59383 | 179 |
| P-e35S | 1 | pMON26180 | 365 |

Both the fusion location and choice of enhancer domain was found to produce a significant effect on promoter activity in tobacco protoplasts. The two promoters with the highest GUS activity were the P-4xAS-1/At.Act1/NsiI (SEQ ID NO: 34) and P-4xAS-1/At.Act1/BsmFI (SEQ ID NO: 35). For constructs comprising the 2xA1B3 enhancer, the highest activity of GUS was shown with the enhancer fused at the BsmFI position. The 2xA1-B3 chimeric promoters were generally less active in all positions when compared to the 4xAS-1 chimeric promoters. Reverse orientation of the enhancer domain did not change significantly the activity of the chimeric promoter.

Example 3

Characterization of Chimeric Promoters in Transgenic Corn Plants

Selected chimeric promoters were used for stable corn plant transformation for reporter expression analysis. Plants were transformed using *agrobacterium*-mediated methods.

In order to have a direct side-by-side comparison of GUS activity in the cytoplasm and CP4 expression in plastids, and to minimize variations in sampling and environmental factors, a few selected chimeric promoter constructs were built. Each test construct comprised the test promoter driving the GUS reporter gene (beta-glucuronidase coding sequence from *E. coli*) and the test promoter driving the CP4 gene (bacterial strain CP4 aroA gene encoding class II EPSPS enzyme) in a linear array. Four test constructs, pMON46172 (P-2xA1-B3/P-Os.Act1-3, SEQ ID NO: 20); pMON46173 (P-4xAS-1/P-Os.Act1-3, SEQ ID NO: 14); pMON46174 (P-4xB3/P-Os.Act1-2, SEQ ID NO: 10); and pMON46175 (P-2xA1-B3/P-Os.Act1-1, SEQ ID NO: 18), and the reference construct, pMON46170 (P-CaMV.E35S driving GUS and P-Os.Act1 driving CP4), were used to transform corn.

Transformed corn plants were selected in glyphosate containing medium. Three R0 plants were generated for each transformation event. The first plant was sprayed with the equivalent of 64 ounce/acre of Roundup® Ultra, the second plant was sprayed with the equivalent of 96 ounce/acre of Roundup® Ultra. The third plant from each event was left as unsprayed control. Ten to fourteen days after Roundup® application each plant was rated for % chlorosis and % malformation. At mid-pollen shed, each R0 plant was rated for male fertility. Positive R0 plants were pollinated with LH198 pollen grains to produce F1 seed.

Transgenic events with single or lowest copy numbers of cassette based on CP4 copy number estimation by Taqman were selected for F1 corn analysis. A total of 5 events from each construct with triplicate plants in each data point were used. The plants were grown in greenhouse from F1 seeds, and selected for positive segregates via glyphosate spray at 16 oz/acre when plants reach V-2 stage. Leaf tissue was taken at V-4 stage, and V-4 again at V-8/V-9 stage. Also at V-8/V-9 stage, tissue was collected from V-8 leaf, root tip, and immature tassel ranging from 0.5 cm-3 cm. Pollen was collected when shedding. Embryo and endosperm were harvested at 12 days after pollination. Several positive embryos were pooled from GUS positive individual kernels. Samples were extracted and used for both GUS quantitative analysis and CP4 ELISA. The P-2xA1-B3/P-Os.Act1-3 and P-4xAS-1/P-Os.Act1-3 chimeric promoters provided GUS gene expression which was as good as or better than that provided by P-CaMV.E35S in most of the tissues analyzed. The P-4xB3/P-Os.Act1-2 and P-2xA1-B3/P-Os.Act1-1 chimeric promoters provided high levels of expression in pollen with moderate or low levels of expression in other tissues as compared to that provided by P-CaMV.E35S. The Data are provided for GUS activity (pmole/min/mg protein) as mean and standard error measurements in Table 5 below.

TABLE 5

F1 Transgenic Corn GUS Activity (pmole/min/mg protein)

| Tissue/Stage | pmon46170 P-CaMV.E35S | | pmon46172 P-2xA1-B3/P-Os.Act1-3 | | pmon46173 P-4xAS-1/P-Os.Act1-3 | | pmon46174 P-4xB3/P-Os.Act1-2 | | pmon46175 P-2xA1-B3/P-Os.Act1-1 | |
|---|---|---|---|---|---|---|---|---|---|---|
| | Mean | SE | Mean | SE | Mean | SE | Mean | SE | Mean | SE |
| Young V4 | 6.54 | 0.29 | 12.28 | 3.00 | 5.11 | 0.75 | 1.02 | 0.35 | 5.70 | 0.60 |
| Aged V4 | 2.82 | 0.85 | 6.47 | 1.43 | 6.78 | 1.59 | 0.10 | 0.02 | 4.14 | 1.09 |
| V8 | 0.67 | 0.20 | 1.27 | 0.51 | 0.64 | 0.12 | 0.17 | 0.05 | 0.13 | 0.01 |
| Tassel | 0.57 | 0.19 | 0.49 | 0.25 | 0.50 | 0.23 | 0.19 | 0.07 | 0.13 | 0.07 |
| Root Tip | 0.38 | 0.04 | 0.84 | 0.10 | 1.11 | 0.43 | 0.19 | 0.04 | 0.97 | 0.38 |
| Pollen | 1.44 | 0.11 | 2.27 | 0.26 | 2.87 | 0.52 | 15.26 | 2.84 | 13.76 | 2.05 |
| Embryo | 2.19 | 0.22 | 2.35 | 0.68 | 5.68 | 1.64 | 1.42 | 0.18 | 2.53 | 0.65 |
| Endosperm | 1.73 | 0.15 | 9.21 | 4.35 | 6.18 | 1.59 | 1.40 | 0.51 | 2.09 | 0.37 |

All four chimeric promoters provided CP4 gene expression which was as good as or better than that provided by P-Os.Act1 in all of the tissues analyzed with the exception of pollen. Expression levels in pollen for chimeric promoter constructs were approximately 20% to 73% that of expression levels in pollen for P-Os.Act1 constructs. Data are provided for CP4 expression levels (μg CP4 protein/g total protein) as mean and standard error measurements in Table 6 below.

TABLE 6

F1 Transgenic Corn CP4 Expression levels (μg CP4 protein/g total protein)

| Tissue/Stage | pmon46170 and P-Os.Act1 | | pmon46172 P-2xA1-B3/P-Os.Act1-3 | | pmon46173 P-4xAS-1/P-Os.Act1-3 | | pmon46174 P-4xB3/P-Os.Act1-2 | | pmon46175 P-2xA1-B3/P-Os.Act1-1 | |
|---|---|---|---|---|---|---|---|---|---|---|
| | Mean | SE | Mean | SE | Mean | SE | Mean | SE | Mean | SE |
| Young V4 | 31 | 3 | 35 | 2 | 408 | 122 | 280 | 66 | 952 | 540 |
| Aged V4 | 20 | 2 | 2187 | 656 | 1802 | 411 | 524 | 257 | 688 | 298 |

TABLE 6-continued

F1 Transgenic Corn CP4 Expression levels (μg CP4 protein/g total protein)

| Tissue/Stage | pmon46170 and P-Os.Act1 | | pmon46172 P-2xA1-B3/P-Os.Act1-3 | | pmon46173 P-4xAS-1/P-Os.Act1-3 | | pmon46174 P-4xB3/P-Os.Act1-2 | | pmon46175 P-2xA1-B3/P-Os.Act1-1 | |
|---|---|---|---|---|---|---|---|---|---|---|
| | Mean | SE | Mean | SE | Mean | SE | Mean | SE | Mean | SE |
| V8 | 17 | 2 | 1055 | 298 | 870 | 272 | 311 | 35 | 284 | 110 |
| Tassel | 225 | 27 | 1334 | 515 | 1002 | 178 | 408 | 31 | 1072 | 303 |
| Root Tip | 89 | 8 | 745 | 185 | 765 | 173 | 184 | 22 | 279 | 68 |
| Pollen | 797 | 97 | 165 | 13 | 217 | 33 | 370 | 16 | 582 | 74 |
| Embryo | 241 | 54 | 623 | 69 | 1101 | 187 | 305 | 69 | 566 | 84 |
| Endosperm | 229 | 21 | 792 | 212 | 889 | 229 | 237 | 36 | 375 | 46 |

The F1 progenies were also used for field tests. Three F1 populations derived from three R0 plants of each event were tested. Commercial Roundup Ready® corn lines GA21 and NK603 were used as positive controls. Three Roundup® rates were used in this test: 0, 96, and 128 oz/A. Roundup® was applied at V4 leaf stage. Data obtained were % transformation efficiency (TE), number of single copy events per total events generated, Leaf CP4 levels (μgCP4/g fresh weight tissue), Pollen CP4 levels (μgCP4/g fresh weight tissue), percent chlorosis (CHL), percent malformation (MAL) at 10-14 DAT (days after treatment), and male fertility score (MFR) measured 1-5 with 5 the highest. Data represent the average score collected across the events generated for each construct and only tasseled plants were included for some measurements. Plants transformed with the P-4xB3/P-Os.Act1-2 or the P-4xAS-1/P-Os.Act1-3 chimeric promoter constructs had chlorosis scores equivalent to the reference construct (pMON46170). P-4xAS-1/P-Os.Act1-3 had a malformation score lower than that of the reference construct. All chimeric promoters tested had male fertility rates comparable to that of plants transformed with the reference construct. Data are provided in Table 7 below.

TABLE 7

Roundup ® Tolerance in Transgenic Corn Field Tests

| Promoter | Construct | % TE | Single Copy | Leaf CP4 | Pollen CP4 | Pollen GUS | % CHL | % MAL | MFR |
|---|---|---|---|---|---|---|---|---|---|
| P-CaMV.E35S and P-Os.Act1 | pMON46170 | 12 | 7/15 | 22 | 1471 | 4.4 | 1 | 1 | 5 |
| P-2xA1-B3/P-Os.Act1-3 | pMON46172 | 10 | 5/15 | 116 | 313 | 5.8 | 7 | 4 | 5 |
| P-4xAS-1/P-Os.Act1-3 | pMON46173 | 16 | 9/15 | 319 | 475 | 9.7 | 1 | 0 | 5 |
| P-4xB3/P-Os.Act1-2 | pMON46174 | 24 | 8/15 | 78 | 674 | 24.3 | 1 | 3 | 5 |
| P-2xA1-B3/P-Os.Act1-1 | pMON46175 | — | 1/15 | 77 | 767 | 34.1 | 2 | 3 | 5 | bidopsis actin 1 promoter (P-At.Act1) were used as controls. Data are provided in Table 8 below

TABLE 8

Transgenic Arabidopsis analysis with chimeric At-Act1 promoters

| Promoter | SEQ ID NO | Construct | Flower | Leaf |
|---|---|---|---|---|
| P-At.Act1 | 8 | pMON59382 | 139 | 62 |
| P-CaMV.e35S | 1 | pMON59381 | 374 | 176 |
| P-2xA1-B3/At.Act1/BstZI | 25 | pMON59378 | 0 | 24 |
| P-4xAS-1/At.Act1/BstZI | 32 | pMON59377 | 12 | 47 |
| P-4xAS-1/At.Act1/ArvII | 30 | pMON59379 | 58 | 18 |
| P-4xAS-1/At.Act1/NsiI | 34 | pMON59375 | 46 | 36 |
| P-4xAS-1/At.Act1/BstZI-R | 33 | pMON59371 | 66 | 21 |
| P-2xA1-B3/At.Act1/NsiI | 27 | pMON59376 | 113 | 56 |
| P-2xA1-B3/At.Act1/BstZI-R | 26 | pMON59372 | 149 | 114 |
| P-4xAS-1/At.Act1/BsmFI | 35 | pMON59373 | 29 | 256 |
| P-2xA1-B3/At.Act1/ArvII | 24 | pMON59380 | 88 | 199 |
| P-2xA1-B3/At.Act1/BsmFI | 29 | pMON59374 | 153 | 193 |

Example 4

Characterization of Chimeric Promoters in Transgenic Dicots

Several constructs were evaluated in transgenic *Arabidopsis* plants for GUS expression. GUS expression in leaf and flower tissue was measured as pM MUG/μg total protein and results were averaged for all the events produced for construct. The CaMV e35S promoter (P-CaMV.e35S) and *Arabidopsis* actin 1 promoter (P-At.Act1) were used as controls.

GUS expression analysis in *Arabidopsis* showed that P-2xA1-B3/At.Act1/BstZI-R (SEQ ID NO: 26) and P-2xA1-B3/At.Act1/BsmFI (SEQ ID NO: 29) provided transgene expression in flowers comparable to that of the P-At.Act1 promoter. The P-2xA1-B3/At.Act1/BstZI-R (SEQ ID NO: 26), P-4xAS-1/At.Act1/BsmFI (SEQ ID NO: 35), P-2xA1-B3/At.Act1/ArvII (SEQ ID NO: 24), and P-2xA1-B3/At.Act1/BsmFI (SEQ ID NO: 29) promoters provided transgene expression in leaves higher than or comparable to the P-At.Act1 and P-CaMV.e35S.

Example 4

Insect Control Analysis in Corn

Two constructs (pMON38858 and pMON38859) were used to generate transgenic corn plants. Transformations were performed using *Agrobacterium* mediated methods. Both constructs contained the 2xA1-B3/P-Os.Act1-3 promoter (SEQ ID NO: 20) operably linked to a nucleotide sequence encoding a Cry2Ab insecticidal protein (U.S. Pat. No. 6,489,542). Several transgenic corn plant lines produced from each construct were analyzed for Cry2Ab protein levels. The 2xA1-B3/P-Os.Act1-3 promoter was found to express the Cry2Ab protein at high levels in corn leaf tissue when compared with standard controls.

Example 5

Glyphosate Tolerance Analysis in Wheat

Three chimeric promoters were tested in transgenic wheat plants. Transgenic wheat plants were generated from each of the single cassette constructs pMON43646 (P-4xAS-1/P-Os.Act1-3, SEQ ID NO: 14), pMON43647 (P-2xA1-B3/P-Os.Act1-2, SEQ ID NO: 19), and pMON43648 (P-2xA1-B3/P-Os.Act1-3, SEQ ID NO: 20). Transformations were performed with *Agrobacterium* in immature Bobwhite embryos. All three constructs contain a single copy of the CP4 EPSPS gene for glyphosate tolerance. The distinguishing element in each construct is the promoter. Events from each single cassette construct were analyzed for vegetative and reproductive tolerance to glyphosate equivalent to the double cassette lead event 33391 (U.S. Patent Publication US20020062503) generated from pMON30139 which contains two copies of the CP4 EPSPS gene driven by the P-e35S and P-Os.Act1 promoters, respectively. Plants were analyzed for glyphosate tolerance, phenotype, copy number, molecular profile, and genome location. Results are provided below.

R0 plants were spray tested for vegetative and reproductive tolerance with 64 oz/A Roundup® Ultra (1.68 kg/ha acid equivalents of glyphosate) prior to jointing. Plants with vegetative damage were discarded. Fertility was estimated by counting the number of seeds in 20 florets from the central portion of the head and reported as % fertility. Data are provided in Table 9 below.

P-CaMV.e35S promoter driving the CP4 gene, produced only 1 of 37 vegetatively tolerant plants with a fertility of >=80%. This data indicates that the e35S promoter is responsible for vegetative expression of CP4 while the rice actin promoter is responsible for reproductive expression of CP4. Results for the single cassette vector containing the three chimeric promoters (pMON43646, pMON43647, and pMON43648) were similar to those for the double cassette vector pMON30139. 73-75% of the total events generated using these three chimeric promoter constructs had vegetative tolerance, and 20-26% of those events had >=80% fertility. Thus, using one of the three chimeric promoters to drive a single copy of the CP4 EPSPS gene produced similar results in R0 tests as double cassette lead event.

In addition to glyphosate tolerance, transformation efficiencies (TE), leaf CP4 levels (μgCP4/mg total protein from R0 wheat plants), and meristem CP4 levels (μgCP4/mg total protein from R0 wheat plants) were measured in R0 plants. Plants transformed with pMON30139 (the double cassette construct) and pMON30159 (P-ScBV see U.S. Pat. No. 6,489,462) were used as controls. Data are provided in Table 10 below.

TABLE 10

CP4 Expression in Transgenic R0 Wheat Plants

| Promoter | Construct | TE | Leaf CP4 | Meristem CP4 |
|---|---|---|---|---|
| P-CaMV.e35S and P-Os.Act1 | pMON30139 | 4% | 2.23 (0.93%) | 4.54 (1.48%) |
| P-ScBV | pMON30159 | 4.50% | 6.99 (1.43%) | 9.7 (1.71%) |
| P-4xAS-1/P-Os.Act1-3 | pMON43646 | 3.30% | 2.13 (.99%) | 3.72 (1.55%) |
| P-2xA1-B3/P-Os.Act1-2 | pMON43647 | 2.90% | 1.41 (1%) | 1.66 (1.23%) |
| P-2xA1-B3/P-Os.Act1-3 | pMON43648 | 2.20% | 4.62 (0.77%) | 5.79 (1.31%) |

R1 seeds were then collected from the R0 plants and advanced to R1 testing. R1 plants were simultaneously tested for glyphosate tolerance and copy number. The transgene copy number for each event was determined by Southern blot and/or TaqMan quantitative PCR analysis. CP4 gene sequences were used as probes for both assays. A good correlation was observed between single copy calls on Southerns and by TaqMan analysis. Single copy events, with good tol-

TABLE 9

Glyphosate Tolerance in Transgenic R0 Wheat Plants

| Promoter | Construct | R0 Events | # Events with Vegetative Tolerance (% of total) | # Events with >= 80% Fertility (% with Veg Tol) |
|---|---|---|---|---|
| P-Os.Act1 | pMON30167 | 63 | 4 (6%) | 2 (50%) |
| P-CaMV.e35S and P-Os.Act1 | pMON30139 | 150 | 104 (69%) | 24 (23%) |
| P-4xAS-1/P-Os.Act1-3 | pMON43646 | 87 | 65 (75%) | 13 (20%) |
| P-2xA1-B3/P-Os.Act1-2 | pMON43647 | 83 | 61 (73%) | 16 (26%) |
| P-2xA1-B3/P-Os.Act1-3 | pMON43648 | 69 | 51 (74%) | 12 (24%) |

Data on the vegetative and reproductive glyphosate tolerance of R0 wheat plants transformed with a single cassette vector containing CP4 driven by the rice actin promoter (pMON30167) and a double cassette vector containing two CP4 genes driven by P-CaMV.e35s and P-Os.Act1 are also provided in Table 15. Wheat transformation experiments that used the P-CaMV.e35 S cassette alone resulted in plants that were vegetatively tolerant but had low fertility. For example plants generated with pMON42411, comprising only the erance to high doses of glyphosate, were advanced to the R2 generation.

Seeds from selected wheat lines advanced to the R2 generation were planted in 2" pots and sprayed with 128 oz/A Roundup at the 3 leaf stage. Retained lines were transferred to larger pots and sprayed again with 128 oz/A at the 6 leaf stage. In an attempt to force differentiation among events an extreme pressure test was devised where plants were sprayed with 512 oz/A of Roundup®. This was repeated four times between the 3 leaf stage and emergence of the flag leaf. Results for the chimeric promoter lines were compared with results for non-transgenic Bobwhite plants, R4 generation lead event plants (line 33391 generated from pMON30139), and R3 generation plants containing the P-ScBV promoter (line TA_S2520 generated from pMON30159). Yield data (grams) and fertility data (as % of total plants) were collected for each line. Data are provided in Table 11 below.

TABLE 11

Pressure Test of R2 Wheat Plants

| Promoter | Construct | Line | Yield (g) | Fertility (%) |
|---|---|---|---|---|
| N/A | N/A | Non-transgenic Bobwhite | 23.1 | 93.5 |
| P-CaMV.e35S and P-Os.Act1 | pMON30139 | 33391 | 24.1 | 91.2 |
| P-ScBV | pMON30159 | TA_S2520 | 21.0 | 87.5 |
| P-2xA1-B3/P-Os.Act1-2 | pMON43647 | TA_S7535 | 22.2 | 91.5 |
| P-2xA1-B3/P-Os.Act1-2 | pMON43647 | TA_S7890 | 23.0 | 95.8 |
| P-2xA1-B3/P-Os.Act1-2 | pMON43647 | TA_S9215 | 21.5 | 95.2 |
| P-4xAS-1/P-Os.Act1-3 | pMON43646 | TA_S9240 | 20.6 | 95.0 |

From this analysis it is apparent that the use of the P-4xAS-1/P-Os.Act1-3 (SEQ ID NO: 14), P-2xA1-B3/P-Os.Act1-2 (SEQ ID NO: 19), and P-2xA1-B3/P-Os.Act1-3 (SEQ ID NO: 20) promoters in plant CP4 expression cassettes confers glyphosate tolerance to vegetative tissues in wheat plants without negatively impacting fertility. In wheat, cassettes containing the rice actin promoter without these elements produce plants with low vegetative tolerance and are not useful for the production of glyphosate tolerant plants. Therefore one advantage of the chimeric promoters in wheat is that vegetative and reproductive tolerance can be achieved without the use of a double CP4 cassette.

Field trails were performed with R4 generation plants to assess the performance of selected lines. Field trails were done at eight US sites with 4 replications each and treatments of 0, 64, and 128 oz/A Roundup® Ultra equivalent. Each treatment was arranged as a separate, randomized complete block in order to collect equivalence data on unsprayed non-transformed Bobwhite plants. All events had vegetative and reproductive tolerance comparable to the lead event 33391 at doses up to 128 oz/A of Roundup® Ultra. Yield was measured in tons/hectar (T/ha). Data are provided in Table 12 below.

TABLE 12

Yield Data from Field Trials of R4 Plants (T/ha)

| Promoter | Construct | Line | 128 oz/A | 64 oz/A | No spray |
|---|---|---|---|---|---|
| P-CaMV.e35S and P-Os.Act1 | pMON30139 | 33391 | 3.52 | 3.58 | 3.63 |
| P-ScBV | pMON30159 | TA_S2520 | 3.78 | 3.79 | 3.69 |
| P-2xA1-B3/P-Os.Act1-2 | pMON43647 | TA_S7535 | 3.72 | 3.68 | 3.51 |
| P-2xA1-B3/P-Os.Act1-2 | pMON43647 | TA_S7890 | 3.79 | 3.72 | 3.70 |
| P-2xA1-B3/P-Os.Act1-2 | pMON43647 | TA_S9215 | 3.59 | 3.57 | 3.42 |
| P-4xAS-1/P-Os.Act1-3 | pMON43646 | TA_S9240 | 3.58 | 3.81 | 3.66 |

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated herein by reference.

We claim:

1. A chimeric promoter comprising a) a promoter enhancer fused with a rice actin 1 gene promoter at the −80 nt position of the rice actin 1 gene promoter, or b) a fragment of the sequence of a) that comprises the enhancer and promoter activity.

2. The chimeric promoter of claim 1 wherein said promoter Enhancer comprises a Cauliflower mosaic virus 35S promoter enhancer.

3. The chimeric promoter of claim 2 wherein said Cauliflower mosaic virus 35S promoter enhancer comprises a nucleic acid sequence selected from the group consisting of SEQ ID NO: 2-6.

4. A construct comprising the chimeric promoter of claim 1 operably linked to a transcribable polynucleotide molecule operably linked to a 3' transcription termination polynucleotide molecule.

5. The construct of claim 4, wherein said transcribable polynucleotide molecule is a marker sequence.

6. The construct of claim 4, wherein said transcribable polynucleotide molecule is a sequence of agronomic interest.

7. The DNA construct of claim 6, wherein said sequence of agronomic interest is a sequence selected from the group consisting of sequences that encode phosphinothricin acetyltransferase, glyphosate resistant 5-enolpyrovylshikimate-3-phosphate synthase, hydroxyphenyl pyruvate dehydrogenase, dalapon dehalogenase, bromoxynil resistant nitrilase, anthranilate synthase, glyphosate oxidoreductase, dicamba monooxygenase, and glyphosate-N-acetyl transferase.

8. A transgenic plant stably transformed with the construct of claim 4.

9. The transgenic plant of claim 8, wherein said transcribable polynucleotide molecule is a sequence of agronomic interest.

10. The transgenic plant of claim 8, wherein said transcribable polynucleotide molecule is a marker sequence.

11. The construct of claim 8, wherein said transcribable polynucleotide molecule is a marker gene.

12. A method of inhibiting weed growth comprising:
  i. planting in a field transgenic plants comprising the chimeric promoter of claim 1 operably linked to a DNA molecule conferring glyphosate tolerance; and
  ii. applying glyphosate to the field at an application rate that inhibits the growth of weeds, wherein the growth and yield of the transgenic plants is not substantially affected by the glyphosate application.

13. The method of claim 12, wherein said DNA molecule conferring glyphosate tolerance is selected from the group consisting of sequences encoding a glyphosate resistant 5-enolpyrovylshikimate-3-phosphate synthase, a glyphosate oxidoreductase, and a glyphosate-N-acetyl transferase.

14. The method of claim 12, wherein the transgenic plants are capable of tolerating an application rate up to 256 ounces/acre.

15. The method of claim 12, wherein the transgenic plants are capable of tolerating an application rate ranging from 8 ounces/acre to 128 ounces/acre.

16. The method of claim 12, wherein the transgenic plants are capable of tolerating an application rate ranging from 32 ounces/acre to 96 ounces/acre.

17. The chimeric promoter of claim 1, comprising a promoter enhancer fused with a rice actin 1 gene promoter at the −80 nt position of the rice actin 1 gene promoter.

18. The chimeric promoter of claim 3, wherein said Cauliflower mosaic virus 35S promoter enhancer comprises a nucleic acid sequence of SEQ ID NO: 2.

19. The chimeric promoter of claim 3, wherein said Cauliflower mosaic virus 35S promoter enhancer comprises a nucleic acid sequence of SEQ ID NO: 3.

20. The chimeric promoter of claim 3, wherein said Cauliflower mosaic virus 35S promoter enhancer comprises a nucleic acid sequence of SEQ ID NO: 4.

21. The chimeric promoter of claim 3, wherein said Cauliflower mosaic virus 35S promoter enhancer comprises a nucleic acid sequence of SEQ ID NO: 5.

22. The chimeric promoter of claim 3, wherein said Cauliflower mosaic virus 35S promoter enhancer comprises a nucleic acid sequence of SEQ ID NO: 6.

* * * * *

UNITED STATES PATENT AND TRADEMARK OFFICE
CERTIFICATE OF CORRECTION

| | | |
|---|---|---|
| PATENT NO. | : 7,838,652 B2 | |
| APPLICATION NO. | : 12/023350 | |
| DATED | : November 23, 2010 | |
| INVENTOR(S) | : Conner et al. | |

It is certified that error appears in the above-identified patent and that said Letters Patent is hereby corrected as shown below:

In claim 11, column 73, line 40, delete "The construct of claim 8, wherein said transcribable polynucleotide molecule is a marker gene" and insert --A seed of said transgenic plant of claim 8, wherein the seed comprises the construct--.

Signed and Sealed this
Thirtieth Day of August, 2011

David J. Kappos
*Director of the United States Patent and Trademark Office*

SEQUENCE LISTING

<160> NUMBER OF SEQ ID NOS: 35

<210> SEQ ID NO 1
<211> LENGTH: 612
<212> TYPE: DNA
<213> ORGANISM: Cauliflower mosaic virus

<400> SEQUENCE: 1

```
ggtccgattg agactttca acaaagggta atatccggaa acctcctcgg attccattgc      60
ccagctatct gtcactttat tgtgaagata gtggaaaagg aaggtggctc ctacaaatgc    120
catcattgcg ataaaggaaa ggccatcgtt gaagatgcct ctgccgacag tggtcccaaa    180
gatggacccc cacccacgag gagcatcgtg aaaaagaag acgttccaac cacgtcttca     240
aagcaagtgg attgatgtga tggtccgatt gagactttc aacaaagggt aatatccgga    300
aacctcctcg gattccattg cccagctatc tgtcacttta ttgtgaagat agtggaaaag    360
gaaggtggct cctacaaatg ccatcattgc gataaaggaa aggccatcgt tgaagatgcc    420
tctgccgaca gtggtcccaa agatggaccc cacccacga ggagcatcgt ggaaaaagaa    480
gacgttccaa ccacgtcttc aaagcaagtg gattgatgtg atatctccac tgacgtaagg    540
gatgacgcac aatcccacta tccttcgcaa gaccctttcct ctatataagg aagttcattt    600
catttggaga gg                                                        612
```

<210> SEQ ID NO 2
<211> LENGTH: 240
<212> TYPE: DNA
<213> ORGANISM: Cauliflower mosaic virus

<400> SEQUENCE: 2

```
catcgttgaa gatgcctctg ccgacagtgg tcccaaagat ggaccccac ccacctcgac      60
catcgttgaa gatgcctctg ccgacagtgg tcccaaagat ggaccccac ccacctcgac     120
catcgttgaa gatgcctctg ccgacagtgg tcccaaagat ggaccccac ccacctcgac     180
catcgttgaa gatgcctctg ccgacagtgg tcccaaagat ggaccccac ccacctcgac     240
```

<210> SEQ ID NO 3
<211> LENGTH: 221
<212> TYPE: DNA
<213> ORGANISM: Cauliflower mosaic virus

<400> SEQUENCE: 3

```
agcttctgac gtaagggatg acgcacctga cgtaagggat gacgcacctg acgtaaggga      60
tgacgcacct gacgtaaggg atgacgcact cgagatcccc atctccactg acgtaaggga    120
tgacgcacaa tcccactatc cttcgcaaga cccttcctct atataaggaa gttcatttca    180
tttggagagg acacgctgac aagctagctt ggctgcaggt a                        221
```

<210> SEQ ID NO 4
<211> LENGTH: 125
<212> TYPE: DNA
<213> ORGANISM: Cauliflower mosaic virus

<400> SEQUENCE: 4

```
catcgtggaa aagaagacg ttccaaccac gtcttcaaag caagtggatt gatgtgataa      60
gctcctcatc gtgaaaaag aagacgttcc aaccacgtct tcaaagcaag tggattgatg    120
tgata                                                                125
```

```
<210> SEQ ID NO 5
<211> LENGTH: 332
<212> TYPE: DNA
<213> ORGANISM: Cauliflower mosaic virus

<400> SEQUENCE: 5
catcgttgaa gatgcctctg ccgacagtgg tcccaaagat ggacccccac ccacgaggag      60
catcgtggaa aagaagacg ttccaaccac gtcttcaaag caagtggatt gatgtgatat     120
ctccactgac gtaagggatg acgcacaatc ccactatcct tcgaggcctc atcgttgaag    180
atgcctctgc cgacagtggt cccaaagatg acccccacc cacgaggagc atcgtggaaa     240
aagaagacgt tccaaccacg tcttcaaagc aagtggattg atgttatatc tccactgacg    300
taagggatga cgcacaatcc cactatcctt cg                                   332

<210> SEQ ID NO 6
<211> LENGTH: 524
<212> TYPE: DNA
<213> ORGANISM: Cauliflower mosaic virus

<400> SEQUENCE: 6
ggtccgatgt gagactttc aacaaagggt aatatccgga aacctcctcg gattccattg       60
cccagctatc tgtcactta ttgtgaagat agtggaaaag aaggtggct cctacaaatg       120 ccatcattgc gataaaggaa aggccatcgt tgaagatgcc tctgccgaca gtggtcccaa     180
agatggaccc ccaccacga ggagcatcgt ggaaaagaa gacgttccaa ccacgtcttc      240
aaagcaagtg gattgatgtg atggtccgat gtgagacttt tcaacaaagg gtaatatccg     300
gaaacctcct cggattccat tgcccagcta tctgtcactt tattgtgaag atagtggaaa     360
aggaaggtgg ctcctacaaa tgccatcatt gcgataaagg aaaggccatc gttgaagatg     420
cctctgccga cagtggtccc aaagatggac ccccacccac gaggagcatc gtggaaaaag    480
aagacgttcc aaccacgtct caaagcaag tggattgatg tgat                       524

<210> SEQ ID NO 7
<211> LENGTH: 921
<212> TYPE: DNA
<213> ORGANISM: Oryza sativa

<400> SEQUENCE: 7
tcgaggtcat tcatatgctt gagaagagag tcgggatagt ccaaaataaa acaaaggtaa      60
gattacctgg tcaaaagtga aaacatcagt taaaggtgg tataaagtaa aatatcggta      120 ataaaggtg gcccaaagtg aaatttactc ttttctacta ttataaaaat tgaggatgtt     180
tttgtcggta ctttgatacg tcattttgt atgaattggt ttttaagttt attcgctttt     240
ggaaatgcat atctgtattt gagtcgggtt ttaagttcgt ttgcttttgt aaatacagag    300
ggatttgtat aagaaatatc tttagaaaaa cccatatgct aatttgacat aattttttgag    360 aaaaatatat attcaggcga attctcacaa tgaacaataa taagattaaa atagcttttcc    420 cccgttgcag cgcatgggta ttttttctag taaaaataaa agataaactt agactcaaaa     480
catttacaaa aacaacccct aaagttccta aagcccaaag tgctatccac gatccatagc     540
aagcccagcc caacccaacc caacccagcc caccccagtc cagccaactg acaatagtc     600 tccacacccc cccactatca ccgtgagttg tccgcacgca ccgcacgtct cgcagccaaa    660 aaaaaaaga aagaaaaaaa agaaaaagaa aaaacagcag gtgggtccgg gtcgtggggg     720
```

```
ccggaaacgc gaggaggatc gcgagccagc gacgaggccg gccctccctc cgcttccaaa    780
gaaacgcccc ccatcgccac tatatacata ccccccctc tcctcccatc ccccaaccc       840 taccaccacc accaccacca cctccacctc ctcccccctc gctgccggac gacgagctcc     900
tcccccctcc ccctccgccg c                                                921

<210> SEQ ID NO 8
<211> LENGTH: 1577
<212> TYPE: DNA
<213> ORGANISM: Arabidopsis thaliana

<400> SEQUENCE: 8
taaatgacat cagatacacg cttgtgaacc atctttaaag tattgatgga ctcttcacta     60
tgaaagctct ctttaaaatt aattttcttt gtacatgtct ctaagcaatg tcaaattaat   120
tagaggtcca aattcaaaaa aatgtcgtat tgaatcattc cattactaaa ttggttcaat   180
gtcagattta aacagcctag ggataattta gtgagatatg agattctact ttcaacatat   240
actaatccta aatctctagc aacttttat ataagctata aatatcatga aaatgtattt    300
taatcgtttc ataatttatg cagtcacact aatggaaaaa aggccaatta ttattatttt    360
cttcagacta taaatgaaaa cataaattaa aatgcagatt agtttaaaat tttaataagt    420
aagtaaaatg cttatagcct tatacaaaat catatttgga agtttctaac attgttgcaa    480
tttgttatca caaatcacag taatatttgt atactaatta gtaattacaa ctatacacaa    540
atttaaatgg gtaatcatat atttgtgtcc agtggattga acaaatatgc tcggcccatg    600
cggaagtaat gccaattttg ggtgagtaaa gcccatgcga aattttcaca taagaaatgc    660
atgctttttg ttttcaacga catgagttgc atgctttttta tcattgctta tatagttgca    720
agtttgcaac tccttgatat ttttttttatg tagacactac taccaccaaa aactttttggt   780 ctgcttattc ttgtttacta tgtaaaaaaa ataaatgaat tgtttatta ctccgatttg     840 atggagtctg gtttatgagg ttttatagcc tttacagaaa attgatagtt acaaaaatat    900
ttttcaaaaa taaagggta aaaccgtcat ttcaagttgt tattgttttg ggggactgga    960
tttgaaatga aatatagaac cggaaaacaa ggtgagccga agtcgaagcc tttggacccg   1020
tttttatatt tactcctccc attcccttct ccttcaatcc ttcctcctc ctcctcccctt    1080 cttcttcttc ccctctttca ttttccagcc actacaaact tttctatctc tacttttttt    1140
cctctcgatt tcaggtactt tttgagaccc tttgttgtga ttttcgaaca cacacccaa    1200 ttacgtttga ttttttgatcc cgcatcgatt tcaattcatc cgtttctgag tttcttttgg    1260
atctgggtgt cttgagctaa tcttttcgat ctgttgttta tcgattttac tcatgcgtat    1320
gttcattaca ccatttgtta tttgtttaat caaccaaaag actcatgttt ttcaaatgtc    1380
tttaatataa ttttttctgat tgaatttttat aatatttaca tgattctgga tccagaatat    1440
ccttcttctt cttccatttt gtcctgtatt gatttgtctt tgaaaaagga ttgttctttg    1500
tatctgtatt ggtgaaaaag gattgttatt tgttgataaa aatttgatct ttaaacaatg   1560
tttggttttg cataaag                                                    1577

<210> SEQ ID NO 9
<211> LENGTH: 1184
<212> TYPE: DNA
<213> ORGANISM: Artificial Sequence
<220> FEATURE:
<223> OTHER INFORMATION: Synthetic promoter sequence

<400> SEQUENCE: 9
```

```
aagctagctt gtcgaccatc gttgaagatg cctctgccga cagtggtccc aaagatggac    60
ccccacccac ctcgaccatc gttgaagatg cctctgccga cagtggtccc aaagatggac   120
ccccacccac ctcgaccatc gttgaagatg cctctgccga cagtggtccc aaagatggac   180
ccccacccac ctcgaccatc gttgaagatg cctctgccga cagtggtccc aaagatggac   240
ccccacccac ctcgacagct tactcgaggt cattcatatg cttgagaaga gagtcgggat   300
agtccaaaat aaacaaagg taagattacc tggtcaaaag tgaaacatc agttaaaagg    360 tggtataaag taaatatcg gtaataaaag gtggcccaaa gtgaaattta ctcttttcta   420
ctattataaa aattgaggat gttttgtcg gtactttgat acgtcatttt tgtatgaatt    480 ggttttaag tttattcgct tttggaaatg catatctgta tttgagtcgg ttttaagtt    540 cgtttgcttt tgtaaataca gagggatttg tataagaaat atctttagaa aaacccatat   600
gctaatttga cataatttt gagaaaaata tatattcagg cgaattctca caatgaacaa    660
taataagatt aaaatagctt tccccccgttg cagcgcatgg gtatttttttc tagtaaaaat   720 aaaagataaa cttagactca aaacatttac aaaaacaacc cctaaagttc ctaaagccca    780
aagtgctatc cacgatccat agcaagccca gcccaaccca acccaaccca gcccacccca    840
gtccagccaa ctggacaata gtctccacac ccccccacta tcaccgtgag ttgtccgcac    900
gcaccgcacg tctcgcagcc aaaaaaaaaa agaaagaaaa aaaagaaaaa gaaaaaacag    960
caggtgggtc cgggtcgtgg gggccggaaa cgcgaggagg atcgcgagcc agcgacgagg   1020
ccggccctcc ctccgcttcc aaagaaacgc ccccatcgc cactatatac ataccccccc   1080
ctctcctccc atccccccaa ccctaccacc accaccacca ccacctccac ctcctcccccc   1140 ctcgctgccg gacgacgagc tcctcccccc tcccctccg ccgc                     1184

<210> SEQ ID NO 10
<211> LENGTH: 1184
<212> TYPE: DNA
<213> ORGANISM: Artificial Sequence
<220> FEATURE:
<223> OTHER INFORMATION: Synthetic promoter sequence

<400> SEQUENCE: 10
aagcttactc gaggtcattc atatgcttga gaagagagtc gggatagtcc aaaataaaac    60
aaaggtaaga ttacctggtc aaaagtgaaa acatcagtta aaaggtggta taaagtaaaa   120
tatcggtaat aaaaggtggc ccaaagtgaa atttactctt ttctactatt ataaaaattg   180
aggatgtttt tgtcggtact ttgatacgtc attttttgtat gaattggttt ttaagtttat   240
tcgcttttgg aaatgcatat ctgtatttga gtcgggtttt aagttcgttt gcttttgtaa   300
atacagaggg atttgtataa gaaatatctt tagaaaaacc catatgctaa tttgacataa   360
tttttgagaa aaatatatat tcaggcgaat tagcttgtcg accatcgttg aagatgcctc   420
tgccgacagt ggtcccaaag atggaccccc acccacctcg accatcgttg aagatgcctc   480
tgccgacagt ggtcccaaag atggaccccc acccacctcg accatcgttg aagatgcctc   540
tgccgacagt ggtcccaaag atggaccccc acccacctcg accatcgttg aagatgcctc   600
tgccgacagt ggtcccaaag atggaccccc acccacctcg acaattctca caatgaacaa    660
taataagatt aaaatagctt tccccccgttg cagcgcatgg gtatttttttc tagtaaaaat   720 aaaagataaa cttagactca aaacatttac aaaaacaacc cctaaagttc ctaaagccca    780
aagtgctatc cacgatccat agcaagccca gcccaaccca acccaaccca gcccacccca    840
```

| | |
|---|---|
| gtccagccaa ctggacaata gtctccacac cccccactar tcaccgtgag ttgtccgcac | 900 |
| gcaccgcacg tctcgcagcc aaaaaaaaaa agaaagaaaa aaaagaaaaa gaaaaaacag | 960 |
| caggtgggtc cgggtcgtgg gggccggaaa cgcgaggagg atcgcgagcc agcgacgagg | 1020 |
| ccggccctcc ctccgcttcc aaagaaacgc ccccatcgc cactatatac ataccccccc | 1080 |
| ctctcctccc atcccccaa ccctaccacc accaccacca ccacctccac ctcctccccc | 1140 |
| ctcgctgccg gacgacgagc tcctcccccc tccccctccg ccgc | 1184 |

<210> SEQ ID NO 11
<211> LENGTH: 1176
<212> TYPE: DNA
<213> ORGANISM: Artificial Sequence
<220> FEATURE:
<223> OTHER INFORMATION: Synthetic promoter sequence

<400> SEQUENCE: 11

| | |
|---|---|
| aagcttactc gaggtcattc atatgcttga gaagagagtc gggatagtcc aaaataaaac | 60 |
| aaaggtaaga ttacctggtc aaaagtgaaa acatcagtta aaaggtggta taaagtaaaa | 120 |
| tatcggtaat aaaaggtggc ccaaagtgaa atttactctt ttctactatt ataaaaattg | 180 |
| aggatgtttt tgtcggtact ttgatacgtc attttttgtat gaattggttt ttaagtttat | 240 |
| tcgcttttgg aaatgcatat ctgtatttga gtcgggtttt aagttcgttt gcttttgtaa | 300 |
| atacagaggg atttgtataa gaaatatctt tagaaaaacc catatgctaa tttgacataa | 360 |
| tttttgagaa aaatatatat tcaggcgaat tctcacaatg aacaataata agattaaaat | 420 |
| agctttcccc cgttgcagcg catgggtatt ttttctagta aaaataaaag ataaacttag | 480 |
| actcaaaaca tttacaaaaa caaccctaa agttcctaaa gcccaaagtg ctatccacga | 540 |
| tccatagcaa gcccagccca acccaaccca acccagccca cccagtcca gccaactgga | 600 |
| caatagtctc cacacccccc cactatcacc gtgagttgtc cgcacgcacc gcacgtctcg | 660 |
| cagccaaaaa aaaaagaaa gaaaaaaaag aaaagaaaa aacagcaggt gggtccgggt | 720 |
| cgtggggcc ggaaacgcga ggaggatcgc gagccagcga cgaggagctt gtcgaccatc | 780 |
| gttgaagatg cctctgccga cagtggtccc aaagatggac ccccacccac ctcgaccatc | 840 |
| gttgaagatg cctctgccga cagtggtccc aaagatggac ccccacccac ctcgaccatc | 900 |
| gttgaagatg cctctgccga cagtggtccc aaagatggac ccccacccac ctcgaccatc | 960 |
| gttgaagatg cctctgccga cagtggtccc aaagatggac ccccacccac ctcgaccct | 1020 |
| ccctccgctt ccaaagaaac gcccccatc gccactatat acatacccccc ccctctcctc | 1080 |
| ccatccccc aaccctacca ccaccaccac caccacctcc acctcctccc cctcgctgc | 1140 |
| cggacgacga gctcctcccc cctcccctc cgccgc | 1176 |

<210> SEQ ID NO 12
<211> LENGTH: 1158
<212> TYPE: DNA
<213> ORGANISM: Artificial Sequence
<220> FEATURE:
<223> OTHER INFORMATION: Synthetic promoter sequence

<400> SEQUENCE: 12

| | |
|---|---|
| aagctagctt ctgacgtaag ggatgacgca cctgacgtaa gggatgacgc acctgacgta | 60 |
| agggatgacg cacctgacgt aagggatgac gcactcgaga tccccatctc cactgacgta | 120 |
| agggatgacg cacaatccca ctatccttcg caagaccctt cctctatata aggaagttca | 180 |
| tttcatttgg agaggacacg ctgacaagct agcttggctg caggtagatc agcttactcg | 240 |

```
aggtcattca tatgcttgag aagagagtcg ggatagtcca aaataaaaca aaggtaagat      300
tacctggtca aaagtgaaaa catcagttaa aaggtggtat aaagtaaaat atcggtaata      360
aaaggtggcc caaagtgaaa tttactcttt tctactatta taaaaattga ggatgttttt      420
gtcggtactt tgatacgtca tttttgtatg aattggtttt taagtttatt cgcttttgga      480
aatgcatatc tgtatttgag tcgggtttta agttcgtttg cttttgtaaa tacagaggga      540
tttgtataag aaatatcttt agaaaaaccc atatgctaat ttgacataat ttttgagaaa      600
aatatatatt caggcgaatt ctcacaatga acaataataa gattaaaata gctttccccc      660
gttgcagcgc atgggtattt tttctagtaa aaataaaaga taaacttaga ctcaaaacat      720
ttacaaaaac aaccccctaaa gttcctaaag cccaaagtgc tatccacgat ccatagcaag      780
cccagcccaa cccaacccaa cccagcccac cccagtccag ccaactggac aatagtctcc      840 acccccccc actatcaccg tgagttgtcc gcacgcaccg cacgtctcgc agccaaaaaa      900 aaaagaaag aaaaaaaga aaagaaaaa acagcaggtg ggtccgggtc gtggggccg      960 gaaacgcgag gaggatcgcg agccagcgac gaggccggcc ctccctccgc ttccaaagaa     1020 acgccccca tcgccactat atacataccc ccccctctcc tcccatcccc ccaaccctac     1080
caccaccacc accaccacct ccacctcctc cccctcgct gccggacgac gagctcctcc     1140
cccctccccc tccgccgc                                                   1158

<210> SEQ ID NO 13
<211> LENGTH: 1158
<212> TYPE: DNA
<213> ORGANISM: Artificial Sequence
<220> FEATURE:
<223> OTHER INFORMATION: Synthetic promoter sequence

<400> SEQUENCE: 13
aagcttactc gaggtcattc atatgcttga gaagagagtc gggatagtcc aaaataaaac       60
aaaggtaaga ttacctggtc aaaagtgaaa acatcagtta aaaggtggta taaagtaaaa      120
tatcggtaat aaaaggtggc ccaaagtgaa atttactctt ttctactatt ataaaaattg      180
aggatgtttt tgtcggtact ttgatacgtc atttttgtat gaattggttt ttaagtttat      240
tcgcttttgg aaatgcatat ctgtatttga gtcgggtttt aagttcgttt gcttttgtaa      300
atacagaggg atttgtataa gaaatatctt tagaaaaacc catatgctaa tttgacataa      360
tttttgagaa aaatatatat tcaggcgaat tagcttctga cgtaagggat gacgcacctg      420
acgtaaggga tgacgcacct gacgtaaggg atgacgcacc tgacgtaagg gatgacgcac      480
tcgagatccc catctccact gacgtaaggg atgacgcaca atcccactat ccttcgcaag      540
acccttcctc tatataagga agttcatttc atttggagag gacacgctga caagctagct      600
tggctgcagg tagatcaatt ctcacaatga acaataataa gattaaaata gctttccccc      660
gttgcagcgc atgggtattt tttctagtaa aaataaaaga taaacttaga ctcaaaacat      720
ttacaaaaac aaccccctaaa gttcctaaag cccaaagtgc tatccacgat ccatagcaag      780
cccagcccaa cccaacccaa cccagcccac cccagtccag ccaactggac aatagtctcc      840 acccccccc actatcaccg tgagttgtcc gcacgcaccg cacgtctcgc agccaaaaaa      900 aaaagaaag aaaaaaaga aaagaaaaa acagcaggtg ggtccgggtc gtggggccg      960 gaaacgcgag gaggatcgcg agccagcgac gaggccggcc ctccctccgc ttccaaagaa     1020 acgccccca tcgccactat atacataccc ccccctctcc tcccatcccc ccaaccctac     1080
```

-continued

| caccaccacc accaccacct ccacctcctc ccccctcgct gccggacgac gagctcctcc | 1140 |
| cccctccccc tccgccgc | 1158 |

<210> SEQ ID NO 14
<211> LENGTH: 1150
<212> TYPE: DNA
<213> ORGANISM: Artificial Sequence
<220> FEATURE:
<223> OTHER INFORMATION: Synthetic promoter sequence

<400> SEQUENCE: 14

| aagcttactc gaggtcattc atatgcttga gaagagagtc gggatagtcc aaaataaaac | 60 |
| aaaggtaaga ttacctggtc aaaagtgaaa acatcagtta aaaggtggta taaagtaaaa | 120 |
| tatcggtaat aaaaggtggc ccaaagtgaa atttactctt ttctactatt ataaaaattg | 180 |
| aggatgtttt tgtcggtact ttgatacgtc attttttgtat gaattggttt ttaagtttat | 240 |
| tcgcttttgg aaatgcatat ctgtatttga gtcgggtttt aagttcgttt gcttttgtaa | 300 |
| atacagaggg atttgtataa gaaatatctt tagaaaaacc catatgctaa tttgacataa | 360 |
| tttttgagaa aaatatatat tcaggcgaat tctcacaatg aacaataata agattaaaat | 420 |
| agcttttcccc cgttgcagcg catgggtatt ttttctagta aaaataaaag ataaacttag | 480 |
| actcaaaaca tttacaaaaa caaccccctaa agttcctaaa gcccaaagtg ctatccacga | 540 |
| tccatagcaa gcccagccca acccaaccca acccagccca ccccagtcca gccaactgga | 600 |
| caatagtctc cacacccccc cactatcacc gtgagttgtc cgcacgcacc gcacgtctcg | 660 |
| cagccaaaaa aaaaagaaa gaaaaaaag aaaagaaaa aacagcaggt gggtccgggt | 720 |
| cgtgggggcc ggaaacgcga ggaggatcgc gagccagcga cgaggagctt ctgacgtaag | 780 |
| ggatgacgca cctgacgtaa gggatgacgc acctgacgta agggatgacg cacctgacgt | 840 |
| aagggatgac gcactcgaga tcccccatctc cactgacgta agggatgacg cacaatccca | 900 |
| ctatccttcg caagaccctt cctctatata aggaagttca tttcatttgg agaggacacg | 960 |
| ctgacaagct agcttggctg caggtagatc ccctccctcc gcttccaaag aaacgccccc | 1020 |
| catcgccact atatacatac cccccctct cctcccatcc cccaaccct accaccacca | 1080 |
| ccaccaccac ctccacctcc tccccctcg ctgccggacg acgagctcct ccccctccc | 1140 |
| cctccgccgc | 1150 |

<210> SEQ ID NO 15
<211> LENGTH: 1065
<212> TYPE: DNA
<213> ORGANISM: Artificial Sequence
<220> FEATURE:
<223> OTHER INFORMATION: Synthetic promoter sequence

<400> SEQUENCE: 15

| aagcttaggc ctcatcgtgg aaaaagaaga cgttccaacc acgtcttcaa agcaagtgga | 60 |
| ttgatgtgat aagctcctca tcgtggaaaa agaagacgtt ccaaccacgt cttcaaagca | 120 |
| agtggattga tgtgataagc ttactcgagg tcattcatat gcttgagaag agagtcggga | 180 |
| tagtccaaaa taaacaaag gtaagattac ctggtcaaaa gtgaaaacat cagttaaaag | 240 |
| gtggtataaa gtaaaatatc ggtaataaaa ggtggcccaa agtgaaattt actcttttct | 300 |
| actattataa aaattgagga tgttttttgtc ggtactttga tacgtcattt ttgtatgaat | 360 |
| tggttttttaa gtttattcgc ttttggaaat gcatatctgt atttgagtcg ggttttaagt | 420 |
| tcgtttgctt ttgtaaatac agagggattt gtataagaaa tatctttaga aaaacccata | 480 |

```
tgctaatttg acataatttt tgagaaaaat atatattcag gcgaattctc acaatgaaca      540
ataataagat taaaatagct ttcccccgtt gcagcgcatg ggtatttttt ctagtaaaaa      600
taaaagataa acttagactc aaaacattta caaaaacaac ccctaaagtt cctaaagccc      660
aaagtgctat ccacgatcca tagcaagccc agcccaaccc aacccaaccc agcccacccc      720
agtccagcca actggacaat agtctccaca cccccccact atcaccgtga gttgtccgca      780
cgcaccgcac gtctcgcagc caaaaaaaaa aagaaagaaa aaaagaaaa agaaaaaaca      840 gcaggtgggt ccgggtcgtg ggggccggaa acgcgaggag gatcgcgagc cagcgacgag      900
gccggccctc cctccgcttc caaagaaacg ccccccatcg ccactatata catacccccc      960
cctctcctcc catccccccca accctaccac caccaccacc accctccacc cctcctcccc     1020
cctcgctgcc ggacgacgag ctcctccccc ctcccctccg ccgc                      1065
```

<210> SEQ ID NO 16
<211> LENGTH: 1073
<212> TYPE: DNA
<213> ORGANISM: Artificial Sequence
<220> FEATURE:
<223> OTHER INFORMATION: Synthetic promoter sequence

<400> SEQUENCE: 16

```
aagcttactc gaggtcattc atatgcttga gaagagagtc gggatagtcc aaaataaaac       60
aaaggtaaga ttacctggtc aaaagtgaaa acatcagtta aaaggtggta taaagtaaaa      120
tatcggtaat aaaaggtggc ccaaagtgaa atttactctt ttctactatt ataaaaattg      180
aggatgtttt tgtcggtact ttgatacgtc attttttgtat gaattggttt ttaagtttat      240
tcgcttttgg aaatgcatat ctgtatttga gtcgggtttt aagttcgttt gcttttgtaa      300
atacagaggg atttgtataa gaaatatctt tagaaaaacc catatgctaa tttgacataa      360
tttttgagaa aaatatatat tcaggcgaat tagcttaggc ctcatcgtgg aaaagaaga      420 cgttccaacc acgtcttcaa agcaagtgga ttgatgtgat aagctcctca tcgtggaaaa      480
agaagacgtt ccaaccacgt cttcaaagca agtggattga tgtgataagc taattctcac      540
aatgaacaat aataagatta aaatagcttt ccccgttgc agcgcatggg tattttttct      600
agtaaaaata aaagataaac ttagactcaa acatttaca aaaacaaccc ctaaagttcc      660
taaagcccaa agtgctatcc acgatccata gcaagcccag cccaacccaa cccaacccag      720
cccaccccag tccagccaac tggacaatag tctccacacc ccccactat caccgtgagt      780 tgtccgcacg caccgcacgt ctcgcagcca aaaaaaaaa gaaagaaaaa aagaaaaag      840 aaaaaacagc aggtgggtcc gggtcgtggg ggccggaaac gcgaggagga tcgcgagcca      900
gcgacgaggc cggccctccc tccgcttcca aagaaacgcc cccatcgcc actatataca      960 tacccccccc tctcctccca tccccccaac cctaccacca ccaccaccac cacctccacc     1020 tcctccccccc tcgctgccgg acgacgagct cctccccctt ccccctccgc cgc          1073
```

<210> SEQ ID NO 17
<211> LENGTH: 1065
<212> TYPE: DNA
<213> ORGANISM: Artificial Sequence
<220> FEATURE:
<223> OTHER INFORMATION: Synthetic promoter sequence

<400> SEQUENCE: 17

```
aagcttactc gaggtcattc atatgcttga gaagagagtc gggatagtcc aaaataaaac       60
```

```
aaaggtaaga ttacctggtc aaaagtgaaa acatcagtta aaggtggta taaagtaaaa        120 tatcggtaat aaaaggtggc ccaaagtgaa atttactctt ttctactatt ataaaaattg        180
aggatgtttt tgtcggtact ttgatacgtc attttttgtat gaattggttt ttaagtttat        240
tcgcttttgg aaatgcatat ctgtatttga gtcgggtttt aagttcgttt gcttttgtaa        300
atacagaggg atttgtataa gaaatatctt tagaaaaacc catatgctaa tttgacataa        360
tttttgagaa aaatatatat tcaggcgaat tctcacaatg aacaataata agattaaaat        420
agctttcccc cgttgcagcg catgggtatt ttttctagta aaaataaaag ataaacttag        480
actcaaaaca tttacaaaaa caaccccctaa agttcctaaa gcccaaagtg ctatccacga        540
tccatagcaa gcccagccca acccaaccca acccagccca ccccagtcca gccaactgga        600
caatagtctc cacacccccc cactatcacc gtgagttgtc cgcacgcacc gcacgtctcg        660
cagccaaaaa aaaaagaaa gaaaaaaag aaaagaaaa aacagcaggt gggtccgggt        720
cgtgggggcc ggaaacgcga ggaggatcgc gagccagcga cgaggagctt aggcctcatc        780
gtggaaaaag aagacgttcc aaccacgtct tcaaagcaag tggattgatg tgataagctc        840
ctcatcgtgg aaaagaaga cgttccaacc acgtcttcaa agcaagtgga ttgatgtgat        900
aagctccctc cctccgcttc caaagaaacg ccccccatcg ccactatata catacccccc        960
cctctcctcc catccccca accctaccac caccaccacc accactcca cctcctcccc       1020 cctcgctgcc ggacgacgag ctcctccccc ctcccctcc gccgc                       1065
```

<210> SEQ ID NO 18
<211> LENGTH: 1273
<212> TYPE: DNA
<213> ORGANISM: Artificial Sequence
<220> FEATURE:
<223> OTHER INFORMATION: Synthetic promoter sequence

<400> SEQUENCE: 18

```
aagcttaggc ctcatcgttg aagatgcctc tgccgacagt ggtcccaaag atggaccccc         60
acccacgagg agcatcgtgg aaaagaagac cgttccaacc acgtcttcaa agcaagtgga        120
ttgatgtgat atctccactg acgtaaggga tgacgcacaa tcccactatc cttcgaggcc        180
tcatcgttga agatgcctct gccgacagtg gtcccaaaga tggaccccca cccacgagga        240
gcatcgtgga aaagaagac gttccaacca cgtcttcaaa gcaagtggat tgatgttata        300
tctccactga cgtaagggat gacgcacaat cccactatcc ttcgaagctt actcgaggtc        360
attcatatgc ttgagaagag agtcgggata gtccaaaata aaacaaaggt aagattacct        420
ggtcaaaagt gaaacatca gttaaaaggt ggtataaagt aaaatatcgg taataaaagg        480
tggcccaaag tgaaatttac tcttttctac tattataaaa attgaggatg ttttttgtcgg        540 tactttgata cgtcattttt gtatgaattg gttttaagt ttattcgctt ttggaaatgc        600
atatctgtat ttgagtcggg ttttaagttc gtttgctttt gtaaatacag agggatttgt        660
ataagaaata tctttagaaa aacccatatg ctaatttgac ataattttg agaaaaatat        720 atattcaggc gaattctcac aatgaacaat aataagatta aaatagcttt ccccgttgc         780 agcgcatggg tatttttct agtaaaaata aagataaac ttagactcaa acatttaca        840 aaacaaccc ctaaagttcc taagcccaa agtgctatcc acgatccata gcaagcccag        900
cccaacccaa cccaacccag cccacccag tccagccaac tggacaatag tctccacacc        960
cccccactat caccgtgagt tgtccgcacg caccgcacgt ctcgcagcca aaaaaaaaa       1020 gaaagaaaaa aagaaaaag aaaaaacagc aggtgggtcc gggtcgtggg ggccggaaac       1080
```

```
gcgaggagga tcgcgagcca gcgacgaggc cggccctccc tccgcttcca aagaaacgcc   1140
ccccatcgcc actatataca taccccccc tctcctccca tccccccaac cctaccacca   1200
ccaccaccac cacctccacc tcctccccc tcgctgccgg acgacgagct cctccccct    1260 ccccctccgc cgc                                                     1273
```

<210> SEQ ID NO 19
<211> LENGTH: 1281
<212> TYPE: DNA
<213> ORGANISM: Artificial Sequence
<220> FEATURE:
<223> OTHER INFORMATION: Synthetic promoter sequence

<400> SEQUENCE: 19

```
aagcttactc gaggtcattc atatgcttga gaagagagtc gggatagtcc aaaataaaac    60
aaaggtaaga ttacctggtc aaaagtgaaa acatcagtta aaaggtggta taaagtaaaa   120
tatcggtaat aaaaggtggc ccaaagtgaa atttactctt ttctactatt ataaaaattg   180
aggatgtttt tgtcggtact ttgatacgtc attttttgtat gaattggttt ttaagtttat   240
tcgcttttgg aaatgcatat ctgtatttga gtcgggtttt aagttcgttt gcttttgtaa   300
atacagaggg atttgtataa gaaatatctt tagaaaaacc catatgctaa tttgacataa   360
tttttgagaa aaatatatat tcaggcgaat tagcttaggc ctcatcgttg aagatgcctc   420
tgccgacagt ggtcccaaag atggaccccc acccacgagg agcatcgtgg aaaagaaga   480 cgttccaacc acgtcttcaa agcaagtgga ttgatgtgat atctccactg acgtaaggga   540
tgacgcacaa tcccactatc cttcgaggcc tcatcgttga agatgcctct gccgacagtg   600
gtcccaaaga tggaccccca cccacgagga gcatcgtgga aaagaagac gttccaacca   660 cgtcttcaaa gcaagtggat tgatgttata tctccactga cgtaagggat gacgcacaat   720
cccactatcc ttcgaagcta attctcacaa tgaacaataa taagattaaa atagctttcc   780
cccgttgcag cgcatgggta tttttctag taaaaataaa agataaactt agactcaaaa   840
catttacaaa acaaccccct aaagttccta agcccaaag tgctatccac gatccatagc   900
aagcccagcc caacccaacc caacccagcc caccccagtc cagccaactg gacaatagtc   960
tccacacccc cccactatca ccgtgagttg tccgcacgca ccgcacgtct cgcagccaaa   1020 aaaaaaaga aagaaaaaaa agaaaagaa aaaacagcag gtgggtccgg gtcgtggggg   1080
ccggaaacgc gaggaggatc gcgagccagc gacgaggccg gccctcctc cgcttccaaa   1140 gaaacgcccc ccatcgccac tatatacata ccccccctc tcctcccatc ccccaaccc   1200 taccaccacc accaccacca cctccacctc ctcccccctc gctgccggac gacgagctcc   1260 tccccctcc ccctccgccg c                                              1281
```

<210> SEQ ID NO 20
<211> LENGTH: 1273
<212> TYPE: DNA
<213> ORGANISM: Artificial Sequence
<220> FEATURE:
<223> OTHER INFORMATION: Synthetic promoter sequence

<400> SEQUENCE: 20

```
aagcttactc gaggtcattc atatgcttga gaagagagtc gggatagtcc aaaataaaac    60
aaaggtaaga ttacctggtc aaaagtgaaa acatcagtta aaaggtggta taaagtaaaa   120
tatcggtaat aaaaggtggc ccaaagtgaa atttactctt ttctactatt ataaaaattg   180
```

```
aggatgtttt tgtcggtact ttgatacgtc attttttgtat gaattggttt ttaagtttat    240
tcgcttttgg aaatgcatat ctgtatttga gtcgggtttt aagttcgttt gcttttgtaa    300
atacagaggg atttgtataa gaaatatctt tagaaaaacc catatgctaa tttgacataa    360 ttttttgagaa aaatatatat tcaggcgaat tctcacaatg aacaataata agattaaaat   420
agctttcccc cgttgcagcg catgggtatt ttttctagta aaaataaaag ataaacttag    480
actcaaaaca tttacaaaaa caaccccctaa agttcctaaa gcccaaagtg ctatccacga   540
tccatagcaa gcccagccca acccaaccca acccagccca cccagtccag gccaactgga    600
caatagtctc cacacccccc cactatcacc gtgagttgtc cgcacgcacc gcacgtctcg    660
cagccaaaaa aaaaaagaaa gaaaaaaaag aaaagaaaa aacagcaggt gggtccgggt     720
cgtgggggcc ggaaacgcga ggaggatcgc gagccagcga cgaggagctt aggcctcatc    780
gttgaagatg cctctgccga cagtggtccc aaagatggac ccccacccac gaggagcatc    840
gtggaaaaag aagacgttcc aaccacgtct caaagcaag tggattgatg tgatatctcc      900
actgacgtaa gggatgacgc acaatcccac tatccttcga ggcctcatcg ttgaagatgc    960
ctctgccgac agtggtccca agatggaccc ccacccacg aggagcatcg tggaaaaga      1020 agacgttcca accacgtctt caaagcaagt ggattgatgt tatatctcca ctgacgtaag    1080
ggatgacgca caatcccact atccttcgaa gctccctccc tccgcttcca agaaacgcc     1140 ccccatcgcc actatataca taccccccccc tctcctccca tcccccccaac cctaccacca  1200 ccaccaccac cacctccacc tcctccccccc tcgctgccgg acgacgagct cctccccccct 1260 cccctccgc cgc                                                        1273

<210> SEQ ID NO 21
<211> LENGTH: 1467
<212> TYPE: DNA
<213> ORGANISM: Artificial Sequence
<220> FEATURE:
<223> OTHER INFORMATION: Synthetic promoter sequence

<400> SEQUENCE: 21
aagctagctt ctgcaggtcc gatgtgagac ttttcaacaa agggtaatat ccggaaacct     60
cctcggattc cattgcccag ctatctgtca ctttattgtg aagatagtgg aaaaggaagg    120
tggctcctac aaatgccatc attgcgataa aggaaaggcc atcgttgaag atgcctctgc    180
cgacagtggt cccaaagatg acccccacc cacgaggagc atcgtggaaa agaagacgt     240 tccaaccacg tcttcaaagc aagtggattg atgtgatggt ccgatgtgag acttttcaac    300
aaagggtaat atccggaaac ctcctcggat tccattgccc agctatctgt cactttattg    360
tgaagatagt ggaaaaggaa ggtggctcct acaaatgcca tcattgcgat aaaggaaagg    420
ccatcgttga agatgcctct gccgacagtg tcccaaaga tggaccccca cccacgagga    480
gcatcgtgga aaagaagac gttccaacca cgtcttcaaa gcaagtggat tgatgtgata   540
gcttactcga ggtcattcat atgcttgaga agagagtcgg atagtccaa ataaaacaa      600 aggtaagatt acctggtcaa aagtgaaaac atcagttaaa aggtggtata agtaaaata   660 tcggtaataa aagtggccc aaagtgaaat ttactctttt ctactattat aaaaattgag    720 gatgttttg tcggtacttt gatacgtcat ttttgtatga attggttttt aagtttattc    780
gcttttggaa atgcatatct gtatttgagt cgggttttaa gttcgtttgc ttttgtaaat    840
acagagggat tgtataaga aatatcttta gaaaaccca tatgctaatt tgacataatt     900
tttgagaaaa atatatattc aggcgaattc tcacaatgaa caataataag attaaaatag    960
```

-continued

```
ctttcccccg ttgcagcgca tgggtatttt ttctagtaaa aataaaagat aaacttagac    1020
tcaaaacatt tacaaaaaca acccctaaag ttcctaaagc ccaaagtgct atccacgatc    1080
catagcaagc ccagcccaac ccacccaac ccagcccacc ccagtccagc caactggaca     1140
atagtctcca cacccccca ctatcaccgt gagttgtccg cacgcaccgc acgtctcgca    1200
gccaaaaaaa aaagaaaga aaaaaagaa aagaaaaaa cagcaggtgg gtccgggtcg     1260 tggggccgg aaacgcgagg aggatcgcga gccagcgacg aggccggccc tccctccgct     1320
tccaaagaaa cgcccccat cgccactata tacatacccc ccctctcct cccatccccc     1380 caaccctacc accaccacca ccaccacctc cacctcctcc cccctcgctg ccggacgacg    1440
agctcctccc ccctcccccct ccgccgc                                      1467
```

<210> SEQ ID NO 22
<211> LENGTH: 1467
<212> TYPE: DNA
<213> ORGANISM: Artificial Sequence
<220> FEATURE:
<223> OTHER INFORMATION: Synthetic promoter sequence

<400> SEQUENCE: 22

```
aagcttactc gaggtcattc atatgcttga gaagagagtc gggatagtcc aaaataaaac      60
aaaggtaaga ttacctggtc aaaagtgaaa acatcagtta aaaggtggta taagtaaaa    120 tatcggtaat aaaaggtggc ccaaagtgaa atttactctt ttctactatt ataaaaattg     180
aggatgtttt tgtcggtact ttgatacgtc atttttgtat gaattggttt ttaagtttat     240
tcgcttttgg aaatgcatat ctgtatttga gtcgggtttt aagttcgttt gcttttgtaa     300
atacagaggg atttgtataa gaatatctt tagaaaaacc catatgctaa tttgacataa     360
tttttgagaa aaatatatat tcaggcgaat tagcttctgc aggtccgatg tgagactttt     420
caacaaaggg taatatccgg aaacctcctc ggattccatt gcccagctat ctgtcacttt     480
attgtgaaga tagtggaaaa ggaaggtggc tcctacaaat gccatcattg cgataaagga     540
aaggccatcg ttgaagatgc ctctgccgac agtggtccca agatggacc cccacccacg      600 aggagcatcg tggaaaaaga agacgttcca accacgtctt caaagcaagt ggattgatgt     660
gatggtccga tgtgagactt tcaacaaagg gtaatatcc ggaaacctcc tcggattcca     720
ttgcccagct atctgtcact ttattgtgaa gatagtggaa aaggaaggtg ctcctacaa     780 atgccatcat tgcgataaag gaaaggccat cgttgaagat gcctctgccg acagtggtcc     840
caaagatgga ccccacccca cgaggagcat cgtggaaaaa gaagacgttc caaccacgtc     900
ttcaaagcaa gtggattgat gtgataattc tcacaatgaa caataataag attaaaatag     960
ctttcccccg ttgcagcgca tgggtatttt ttctagtaaa aataaaagat aaacttagac    1020
tcaaaacatt tacaaaaaca acccctaaag ttcctaaagc ccaaagtgct atccacgatc    1080
catagcaagc ccagcccaac ccacccaac ccagcccacc ccagtccagc caactggaca     1140
atagtctcca cacccccca ctatcaccgt gagttgtccg cacgcaccgc acgtctcgca    1200
gccaaaaaaa aaagaaaga aaaaaagaa aagaaaaaa cagcaggtgg gtccgggtcg     1260 tggggccgg aaacgcgagg aggatcgcga gccagcgacg aggccggccc tccctccgct     1320
tccaaagaaa cgcccccat cgccactata tacatacccc ccctctcct cccatccccc     1380 caaccctacc accaccacca ccaccacctc cacctcctcc cccctcgctg ccggacgacg    1440
agctcctccc ccctcccccct ccgccgc                                      1467
```

<210> SEQ ID NO 23
<211> LENGTH: 1459
<212> TYPE: DNA
<213> ORGANISM: Artificial Sequence
<220> FEATURE:
<223> OTHER INFORMATION: Artificial promoter sequence

<400> SEQUENCE: 23

```
aagcttactc gaggtcattc atatgcttga gaagagagtc gggatagtcc aaaataaaac      60
aaaggtaaga ttacctggtc aaaagtgaaa acatcagtta aaaggtggta taaagtaaaa     120
tatcggtaat aaaaggtggc ccaaagtgaa atttactctt ttctactatt ataaaaattg     180
aggatgtttt tgtcggtact ttgatacgtc attttttgtat gaattggttt ttaagtttat     240
tcgcttttgg aaatgcatat ctgtatttga gtcgggtttt aagttcgttt gcttttgtaa     300
atacagaggg atttgtataa gaaatatctt tagaaaaacc catatgctaa tttgacataa     360
tttttgagaa aaatatatat tcaggcgaat tctcacaatg aacaataata agattaaaat     420
agctttcccc cgttgcagcg catgggtatt ttttctagta aaaataaaag ataaacttag     480
actcaaaaca tttacaaaaa caaccctaa agttcctaaa gcccaaagtg ctatccacga     540
tccatagcaa gcccagccca acccaaccca acccagccca ccccagtcca gccaactgga     600
caatagtctc cacacccccc cactatcacc gtgagttgtc cgcacgcacc gcacgtctcg     660
cagccaaaaa aaaaagaaa gaaaaaaaag aaaagaaaa aacagcaggt gggtccgggt     720
cgtgggggcc ggaaacgcga ggaggatcgc gagccagcga cgaggagctt ctgcaggtcc     780
gatgtgagac ttttcaacaa agggtaatat ccggaaacct cctcggattc cattgcccag     840
ctatctgtca ctttattgtg aagatagtgg aaaaggaagg tggctcctac aaatgccatc     900
attgcgataa aggaaaggcc atcgttgaag atgcctctgc cgacagtggt cccaaagatg     960
gacccccacc cacgaggagc atcgtggaaa agaagacgt tccaaccacg tcttcaaagc    1020
aagtggattg atgtgatggt ccgatgtgag acttttcaac aaagggtaat atccggaaac    1080
ctcctcggat tccattgccc agctatctgt cactttattg tgaagatagt ggaaaaggaa    1140
ggtggctcct acaaatgcca tcattgcgat aaaggaaagg ccatcgttga agatgcctct    1200
gccgacagtg gtcccaaaga tggacccccca cccacgagga gcatcgtgga aaagaagac    1260
gttccaacca cgtcttcaaa gcaagtggat tgatgtgatc cctccctccg cttccaaaga    1320
aacgcccccc atcgccacta tatacatacc cccccctctc ctcccatccc ccaaccccta    1380
ccaccaccac caccaccacc tccacctcct cccccctcgc tgccggacga cgagctcctc    1440
cccctcccc ctccgccgc                                                 1459
```

<210> SEQ ID NO 24
<211> LENGTH: 1939
<212> TYPE: DNA
<213> ORGANISM: Artificial Sequence
<220> FEATURE:
<223> OTHER INFORMATION: Synthetic promoter sequence

<400> SEQUENCE: 24

```
taaatgacat cagatacacg cttgtgaacc atctttaaag tattgatgga ctcttcacta      60
tgaaagctct ctttaaaatt aattttcttt gtacatgtct ctaagcaatg tcaaattaat     120
tagaggtcca aattcaaaaa aatgtcgtat tgaatcattc cattactaaa ttggttcaat     180
gtcagattta aacagcctag agcttaggcc tcatcgttga agatgcctct gccgacagtg     240
gtcccaaaga tggacccccca cccacgagga gcatcgtgga aaagaagac gttccaacca     300
```

```
cgtcttcaaa gcaagtggat tgatgtgata tctccactga cgtaagggat gacgcacaat      360
cccactatcc ttcgaggcct catcgttgaa gatgcctctg ccgacagtgg tcccaaagat      420
ggacccccac ccacgaggag catcgtggaa aaagaagacg ttccaaccac gtcttcaaag      480
caagtggatt gatgttatat ctccactgac gtaagggatg acgcacaatc ccactatcct      540
tcgaagctct agggataatt tagtgagata tgagattcta ctttcaacat atactaatcc      600
taaatctcta gcaacttttt atataagcta taaatatcat gaaaatgtat tttaatcgtt      660
tcataattta tgcagtcaca ctaatggaaa aaggccaat tattattatt tcttcagac       720 tataaatgaa aacataaatt aaaatgcaga ttagtttaaa attttaataa gtaagtaaaa      780
tgcttatagc cttatacaaa atcatatttg gaagtttcta acattgttgc aatttgttat      840
cacaaatcac agtaatattt gtatactaat tagtaattac aactatacac aaatttaaat      900
gggtaatcat atatttgtgt ccagtggatt gaacaaatat gctcggccca tgcggaagta      960
atgccaattt tgggtgagta agcccatgc gaaattttca cataagaaat gcatgctttt     1020
tgttttcaac gacatgagtt gcatgctttt tatcattgct tatatagttg caagtttgca     1080
actccttgat atttttttta tgtagacact actaccacca aaaactttg gtctgcttat      1140 tcttgtttac tatgtaaaaa aaataaatga attgtttatt tactccgatt tgatggagtc     1200
tggtttatga ggttttatag cctttacaga aaattgatag ttacaaaaat attttcaaa      1260 aataaagggg taaaaccgtc atttcaagtt gttattgttt tggggactg gatttgaaat      1320 gaaatataga accggaaaac aaggtgagcc gaagtcgaag cctttggacc cgtttttata     1380
tttactcctc ccattccctt ctccttcaat ccttccttcc tcctcctccc ttcttcttct     1440
tcccctcttt cattttccag ccactacaaa cttttctatc tctactttt ttcctctcga      1500 tttcaggtac tttttgagac cctttgttgt gattttcgaa cacacacccc aattacgttt     1560 gattttgat cccgcatcga tttcaattca tccgtttctg agtttctttt ggatctgggt      1620
gtcttgagct aatcttttcg atctgttgtt tatcgatttt actcatgcgt atgttcatta     1680
caccatttgt tatttgttta atcaaccaaa agactcatgt ttttcaaatg tctttaatat     1740 aattttctg attgaatttt ataatattta catgattctg gatccagaat atccttcttc      1800
ttcttccatt ttgtcctgta ttgatttgtc tttgaaaaag gattgttctt tgtatctgta     1860
ttggtgaaaa aggattgtta tttgttgata aaaatttgat ctttaaacaa tgtttggttt     1920
tgcataaagg tagaagacc                                                  1939
```

<210> SEQ ID NO 25
<211> LENGTH: 1935
<212> TYPE: DNA
<213> ORGANISM: Artificial Sequence
<220> FEATURE:
<223> OTHER INFORMATION: Synthetic promoter sequence

<400> SEQUENCE: 25

```
taaatgacat cagatacacg cttgtgaacc atctttaaag tattgatgga ctcttcacta       60
tgaaagctct cttttaaaatt aatttcttt gtacatgtct ctaagcaatg tcaaattaat      120
tagaggtcca aattcaaaaa aatgtcgtat tgaatcattc cattactaaa ttggttcaat      180
gtcagattta aacagcctag ggataattta gtgagatatg agattctact ttcaacatat      240
actaatccta aatctctagc aacttttat ataagctata aatatcatga aaatgtattt       300
taatcgtttc ataatttatg cagtcacact aatggaaaaa aggccaatta ttattatttt      360
```

```
cttcagacta taaatgaaaa cataaattaa aatgcagatt agtttaaaat tttaataagt      420
aagtaaaatg cttatagcct tatacaaaat catatttgga agttctaac attgttgcaa       480 tttgttatca caaatcacag taatatttgt aagcttaggc ctcatcgttg aagatgcctc      540
tgccgacagt ggtcccaaag atggaccccc acccacgagg agcatcgtgg aaaaagaaga      600
cgttccaacc acgtcttcaa agcaagtgga ttgatgtgat atctccactg acgtaaggga      660
tgacgcacaa tcccactatc cttcgaggcc tcatcgttga agatgcctct gccgacagtg      720
gtcccaaaga tggaccccca cccacgagga gcatcgtgga aaaagaagac gttccaacca      780
cgtcttcaaa gcaagtggat tgatgttata tctccactga cgtaagggat gacgcacaat      840
cccactatcc ttcgaagctt actaattagt aattacaact atacacaaat ttaaatgggt      900
aatcatatat ttgtgtccag tggattgaac aaatatgctc ggcccatgcg gaagtaatgc      960
caattttggg tgagtaaagc ccatgcgaaa ttttcacata agaaatgcat gcttttgtt      1020 ttcaacgaca tgagttgcat gcttttatc attgcttata tagttgcaag tttgcaactc      1080
cttgatattt tttttatgta gacactacta ccaccaaaaa cttttggtct gcttattctt      1140
gtttactatg taaaaaaaat aaatgaattg tttatttact ccgatttgat ggagtctggt      1200
ttatgaggtt ttatagcctt tacagaaaat tgatagttac aaaaatattt ttcaaaaata      1260
aaagggtaaa accgtcattt caagttgtta ttgtttttggg ggactggatt tgaaatgaaa     1320
tatagaaccg gaaaacaagg tgagccgaag tcgaagcctt tggacccgtt tttatattta      1380
ctcctcccat tcccttctcc ttcaatcctt ccttcctcct cctcccttct tcttcttccc      1440
ctctttcatt ttccagccac tacaaacttt tctatctcta ctttttttcc tctcgatttc      1500
aggtactttt tgagacccctt tgttgtgatt ttcgaacaca cacccaatt acgtttgatt      1560 tttgatcccg catcgatttc aattcatccg tttctgagtt tcttttggat ctgggtgtct      1620
tgagctaatc ttttcgatct gttgtttatc gattttactc atgcgtatgt tcattacacc      1680
atttgttatt tgtttaatca accaaaagac tcatgttttt caaatgtctt taatataatt      1740
tttctgattg aatttttataa tatttacatg attctggatc cagaatatcc ttcttctttct     1800 tccattttgt cctgtattga tttgtctttg aaaaaggatt gttctttgta tctgtattgg      1860
tgaaaaagga ttgttatttg ttgataaaaa tttgatctt aaacaatgtt tggttttgca      1920
taaaggtaga agacc                                                       1935

<210> SEQ ID NO 26
<211> LENGTH: 1935
<212> TYPE: DNA
<213> ORGANISM: Artificial Sequence
<220> FEATURE:
<223> OTHER INFORMATION: Synthetic promoter sequence

<400> SEQUENCE: 26
taaatgacat cagatacacg cttgtgaacc atctttaaag tattgatgga ctcttcacta       60
tgaaagctct ctttaaaatt aattttcttt gtacatgtct ctaagcaatg tcaaattaat      120
tagaggtcca aattcaaaaa aatgtcgtat tgaatcattc cattactaaa ttggttcaat      180
gtcagattta aacagcctag ggataattta gtgagatatg agattctact ttcaacatat      240
actaatccta aatctctagc aactttttat ataagctata aatatcatga aaatgtattt      300
taatcgtttc ataatttatg cagtcacact aatggaaaaa aggccaatta ttattatttt      360
cttcagacta taaatgaaaa cataaattaa aatgcagatt agtttaaaat tttaataagt      420
aagtaaaatg cttatagcct tatacaaaat catatttgga agttctaac attgttgcaa       480
```

```
tttgttatca caaatcacag taatatttgt aagcttcgaa ggatagtggg attgtgcgtc      540
atcccttacg tcagtggaga tataacatca atccacttgc tttgaagacg tggttggaac      600
gtcttctttt tccacgatgc tcctcgtggg tggggtccca tctttgggac cactgtcggc      660
agaggcatct tcaacgatga ggcctcgaag gatagtggga ttgtgcgtca tcccttacgt      720
cagtggagat atcacatcaa tccacttgct ttgaagacgt ggttggaacg tcttcttttt      780
ccacgatgct cctcgtgggt ggggtccat ctttgggacc actgtcggca gaggcatctt      840
caacgatgag gcctaagctt actaattagt aattacaact atacacaaat ttaaatgggt      900
aatcatatat ttgtgtccag tggattgaac aaatatgctc ggcccatgcg aagtaatgc       960 caattttggg tgagtaaagc ccatgcgaaa ttttcacata agaaatgcat gcttttgtt      1020 ttcaacgaca tgagttgcat gcttttttatc attgcttata tagttgcaag tttgcaactc     1080
cttgatattt ttttatgta gacactacta ccaccaaaaa cttttggtct gcttattctt      1140
gtttactatg taaaaaaaat aaatgaattg tttatttact ccgatttgat ggagtctggt      1200
ttatgaggtt ttatagcctt tacagaaaat tgatagttac aaaaatatttt ttcaaaaata    1260 aaagggtaaa accgtcattt caagttgtta ttgttttggg ggactggatt tgaaatgaaa     1320
tatagaaccg gaaaacaagg tgagccgaag tcgaagcctt tggacccgtt tttatattta    1380
ctcctcccat tcccttctcc ttcaatcctt ccttcctcct cctcccttct tcttcttccc     1440
ctctttcatt ttccagccac tacaaactt tctatctcta cttttttttcc tctcgatttc    1500 aggtacttt tgagaccctt tgttgtgatt ttcgaacaca cacccaaatt acgtttgatt     1560
tttgatcccg catcgatttc aattcatccg tttctgagtt tcttttggat ctgggtgtct    1620
tgagctaatc ttttcgatct gttgtttatc gattttactc atgcgtatgt tcattacacc     1680
atttgttatt tgtttaatca accaaaagac tcatgttttt caaatgtctt taatataatt     1740
tttctgattg aattttataa tatttacatg attctggatc cagaatatcc ttcttcttct     1800
tccattttgt cctgtattga tttgtctttg aaaaaggatt gttctttgta tctgtattgg     1860
tgaaaaagga ttgttatttg ttgataaaaa tttgatcttt aaacaatgtt tggttttgca    1920
taaaggtaga agacc                                                     1935
```

<210> SEQ ID NO 27
<211> LENGTH: 1963
<212> TYPE: DNA
<213> ORGANISM: Artificial Sequence
<220> FEATURE:
<223> OTHER INFORMATION: Synthetic promoter sequence

<400> SEQUENCE: 27

```
ggccgcctgc aggaagctgt acccccccaag cttaaatgac atcagataca cgcttgtgaa     60
ccatctttaa agtattgatg gactcttcac tatgaaagct ctctttaaaa ttaatttttct   120 ttgtacatgt ctctaagcaa tgtcaaatta attagaggtc caaattcaaa aaaatgtcgt    180
attgaatcat tccattacta aattggttca atgtcagatt taaacagcct agggataatt   240
tagtgagata tgagattcta ctttcaacat atactaatcc taaatctcta gcaactttttt 300 atataagcta taaatatcat gaaaatgtat tttaatcgtt tcataattta tgcagtcaca    360
ctaatggaaa aaaggccaat tattattatt ttcttcgac tataaatgaa aacataaatt     420
aaaatgcaga ttagttttaaa attttaataa gtaagtaaaa tgcttatagc cttatacaaa   480
atcatatttg gaagtttcta acattgttgc aatttgttat cacaaatcac agtaaatattt   540
```

```
gtatactaat tagtaattac aactatacac aaatttaaat gggtaatcat atatttgtgt      600
ccagtggatt gaacaaatat gctcggccca tgcggaagta atgccaattt tgggtgagta      660
aagcccatgc gaaattttca cataagaaaa gcttaggcct catcgttgaa gatgcctctg      720
ccgacagtgg tcccaaagat ggaccccccac ccacgaggag catcgtggaa aaagaagacg     780
ttccaaccac gtcttcaaag caagtggatt gatgtgatat ctccactgac gtaagggatg      840
acgcacaatc ccactatcct tcgaggcctc atcgttgaag atgcctctgc cgacagtggt      900
cccaaagatg gaccccccacc cacgaggagc atcgtggaaa aagaagacgt tccaaccacg     960
tcttcaaagc aagtggattg atgttatatc tccactgacg taagggatga cgcacaatcc    1020
cactatcctt cgaagcttgc ttttttgtttt caacgacatg agttgcatgc tttttatcat    1080
tgcttatata gttgcaagtt tgcaactcct tgatattttt tttatgtaga cactactacc    1140
accaaaaact tttggtctgc ttattcttgt ttactatgta aaaaaaataa atgaattgtt    1200
tatttactcc gatttgatgg agtctggttt atgaggtttt atagccttta cagaaaattg    1260
atagttacaa aaatattttt caaaaataaa agggtaaaac cgtcatttca agttgttatt    1320
gttttggggg actggatttg aaatgaaata tagaaccgga aaacaaggtg agccgaagtc    1380
gaagcctttg gacccgtttt tatatttact cctcccattc ccttctcctt caatccttcc    1440
ttcctcctcc tcccttcttc ttcttcccct ctttcatttt ccagccacta caaacttttc    1500
tatctctact tttttttcctc tcgatttcag gtacttttttg agacccttttg ttgtgattttt    1560 cgaacacaca ccccaattac gtttgatttt tgatcccgca tcgatttcaa ttcatccgtt    1620
tctgagtttc ttttggatct gggtgtcttg agctaatctt ttcgatctgt tgtttatcga    1680
ttttactcat gcgtatgttc attacaccat ttgttatttg tttaatcaac caaaagactc    1740
atgtttttca aatgtcttta atataatttt tctgattgaa tttttataata tttacatgat    1800 tctggatcca gaatatcctt cttcttcttc catttttgtcc tgtattgatt tgtcttttgaa    1860 aaaggattgt tctttgtatc tgtattggtg aaaaaggatt gttatttgtt gataaaaatt    1920
tgatctttaa acaatgtttg gttttgcata aaggtagaag acc                       1963
```

<210> SEQ ID NO 28
<211> LENGTH: 1963
<212> TYPE: DNA
<213> ORGANISM: Artificial Sequence
<220> FEATURE:
<223> OTHER INFORMATION: Synthetic promoter sequence

<400> SEQUENCE: 28

```
ggccgcctgc aggaagctgt acccccccaag cttaaatgac atcagataca cgcttgtgaa     60
ccatctttaa agtattgatg gactcttcac tatgaaagct ctctttaaaa ttaattttct    120
ttgtacatgt ctctaagcaa tgtcaaatta attagaggtc caaattcaaa aaatgtcgt    180 attgaatcat tccattacta aattggttca atgtcagatt taaacagcct agggataatt    240
tagtgagata tgagattcta ctttcaacat atactaatcc taaatctcta gcaacttttt    300
atataagcta taaatatcat gaaaatgtat tttaatcgtt tcataattta tgcagtcaca    360
ctaatggaaa aaaggccaat tattattatt ttcttcagac tataaatgaa aacataaatt    420
aaaatgcaga ttagtttaaa attttaataa gtaagtaaaa tgcttatagc cttatacaaa    480
atcatatttg gaagtttcta acattgttgc aatttgttat cacaaatcac agtaatattt    540
gtatactaat tagtaattac aactatacac aaatttaaat gggtaatcat atatttgtgt    600
ccagtggatt gaacaaatat gctcggccca tgcggaagta atgccaattt tgggtgagta    660
```

```
aagcccatgc gaaatttca cataagaaaa gcttcgaagg atagtgggat tgtgcgtcat      720
cccttacgtc agtggagata taacatcaat ccacttgctt tgaagacgtg gttggaacgt      780
cttctttttc cacgatgctc ctcgtgggtg ggggtccatc tttgggacca ctgtcggcag      840
aggcatcttc aacgatgagg cctcgaagga tagtgggatt gtgcgtcatc ccttacgtca      900
gtggagatat cacatcaatc cacttgcttt gaagacgtgg ttggaacgtc ttcttttcc       960 acgatgctcc tcgtgggtgg gggtccatct ttgggaccac tgtcggcaga ggcatcttca     1020
acgatgaggc taagcttgc tttttgtttt caacgacatg agttgcatgc tttttatcat       1080
tgcttatata gttgcaagtt tgcaactcct tgatatttt tttatgtaga cactactacc      1140
accaaaaact tttggtctgc ttattcttgt ttactatgta aaaaaataa atgaattgtt      1200 tatttactcc gatttgatgg agtctggttt atgaggtttt atagccttta cagaaaattg      1260
atagttacaa aaatattttt caaaaataaa agggtaaaac cgtcatttca agttgttatt     1320
gttttggggg actggatttg aaatgaaata tagaaccgga aaacaaggtg agccgaagtc     1380
gaagcctttg gacccgtttt tatatttact cctcccattc ccttctcctt caatccttcc     1440
ttcctcctcc tcccttcttc ttcttcccct ctttcattt ccagccacta caaacttttc      1500
tatctctact ttttttcctc tcgatttcag gtacttttg agacccttg ttgtgatttt        1560 cgaacacaca ccccaattac gttgatttt tgatcccgca tcgatttcaa ttcatccgtt      1620
tctgagtttc ttttggatct gggtgtcttg agctaatctt ttcgatctgt tgtttatcga     1680
ttttactcat gcgtatgttc attacaccat ttgttatttg tttaatcaac caaaagactc     1740 atgttttca aatgtcttta atataatttt tctgattgaa ttttataata tttacatgat       1800
tctggatcca gaatatcctt cttcttcttc cattttgtcc tgtattgatt tgtctttgaa     1860
aaaggattgt tctttgtatc tgtattggtg aaaaaggatt gttatttgtt gataaaaatt     1920
tgatctttaa acaatgtttg gttttgcata aaggtagaag acc                      1963

<210> SEQ ID NO 29
<211> LENGTH: 1971
<212> TYPE: DNA
<213> ORGANISM: Artificial Sequence
<220> FEATURE:
<223> OTHER INFORMATION: Synthetic promoter sequence

<400> SEQUENCE: 29
ggccgcctgc aggaagctgt acccccaag cttaaatgac atcagataca cgcttgtgaa        60
ccatctttaa agtattgatg gactcttcac tatgaaagct ctctttaaaa ttaattttct      120
ttgtacatgt ctctaagcaa tgtcaaatta ttagaggtc caattcaaa aaatgtcgt        180 attgaatcat tccattacta aattggttca atgtcagatt taaacagcct agggataatt      240
tagtgagata tgagattcta cttcaacat atactaatcc taaatctcta gcaacttttt      300
atataagcta taaatatcat gaaaatgtat tttaatcgtt tcataattta tgcagtcaca     360
ctaatggaaa aaaggccaat tattattatt ttccttcagac tataaatgaa aacataaatt     420
aaaatgcaga ttagtttaaa attttaataa gtaagtaaaa tgcttatagc cttatacaaa     480
atcatatttg gaagtttcta acattgttgc aattgttat cacaaatcac agtaatattt      540
gtatactaat tagtaattac aactatacac aaatttaaat gggtaatcat atatttgtgt     600
ccagtggatt gaacaaatat gctcggccca tgcggaagta atgccaattt tgggtgagta     660
aagcccatgc gaaattttca cataagaaat gcatgctttt tgtttcaac gacatgagtt      720
```

```
gcatgcttttt tatcattgct tatatagttg caagtttgca actccttgat attttttta      780 tgtagacact actaccacca aaaacttttg gtctgcttat tcttgtttac tatgtaaaaa      840
aaataaatga attgtttatt tactccgatt tgatggagtc tggtttatga ggttttatag      900
cctttacaga aaattgatag ttacaaaaat attttttcaaa aataaaaggg taaaaccgtc     960
atttcaagtt gttattgttt tggggggactg gatttgaaat gaagcttagg cctcatcgtt    1020
gaagatgcct ctgccgacag tggtcccaaa gatggacccc cacccacgag gagcatcgtg    1080
gaaaaagaag acgttccaac cacgtcttca aagcaagtgg attgatgtga tatctccact    1140
gacgtaaggg atgacgcaca atcccactat ccttcgaggc ctcatcgttg aagatgcctc    1200
tgccgacagt ggtcccaaag atggaccccc acccacgagg agcatcgtgg aaaaagaaga    1260
cgttccaacc acgtcttcaa agcaagtgga ttgatgttat atctccactg acgtaaggga    1320
tgacgcacaa tcccactatc cttcgaagct atgaaatata gaaccggaaa acaaggtgag    1380
ccgaagtcga agcctttgga cccgttttta tatttactcc tcccattccc ttctccttca    1440
atccttcctt cctcctcctc ccttcttctt cttcccctct ttcattttcc agccactaca    1500
aacttttcta tctctacttt ttttcctctc gatttcaggt actttttgag acccttgtt    1560 gtgattttcg aacacacacc ccaattacgt ttgattttg atcccgcatc gatttcaatt    1620
catccgtttc tgagtttctt ttggatctgg gtgtcttgag ctaatctttt cgatctgttg    1680
tttatcgatt ttactcatgc gtatgttcat tacaccatt gttatttgtt taatcaacca    1740
aaagactcat gttttcaaa tgtctttaat ataattttc tgattgaatt ttataatatt    1800
tacatgattc tggatccaga atatccttct tcttcttcca ttttgtcctg tattgatttg    1860
tctttgaaaa aggattgttc tttgtatctg tattggtgaa aaaggattgt tatttgttga    1920
taaaaatttg atctttaaac aatgtttggt tttgcataaa ggtagaagac c              1971
```

<210> SEQ ID NO 30
<211> LENGTH: 1816
<212> TYPE: DNA
<213> ORGANISM: Artificial Sequence
<220> FEATURE:
<223> OTHER INFORMATION: Synthetic promoter sequence

<400> SEQUENCE: 30

```
taaatgacat cagatacacg cttgtgaacc atctttaaag tattgatgga ctcttcacta      60
tgaaagctct ctttaaaatt aattttcttt gtacatgtct ctaagcaatg tcaaattaat     120
tagaggtcca aattcaaaaa aatgtcgtat tgaatcattc cattactaaa ttggttcaat     180
gtcagattta aacagcctag agcttctgac gtaagggatg acgcacctga cgtaagggat     240
gacgcacctg acgtaaggga tgacgcacct gacgtaaggg atgacgcact cgagatcccc    300
atctccactg acgtaaggga tgacgcacaa tcccactatc cttcgcaaga cccttcctct    360
atataaggaa gttcatttca tttggagagg acacgctgac aagctagctt ggctgcaggt    420
agatcctagg gataaattag tgagatatga gattctactt tcaacatata ctaatcctaa    480
atctctagca acttttatata taagctataa atatcatgaa aatgtatttt aatcgtttca    540
taatttatgc agtcacacta atggaaaaaa ggccaattat tattatttc ttcagactat     600 aaatgaaaac ataaattaaa atgcagatta gtttaaaatt ttaataagta agtaaaatgc    660
ttatagcctt atacaaaatc atatttggaa gtttctaaca ttgttgcaat tgttatcac     720 aaatcacagt aatatttgta tactaattag taattacaac tatacacaaa tttaaatggg    780
taatcatata tttgtgtcca gtggattgaa caaatatgct cggcccatgc ggaagtaatg    840
```

```
ccaattttgg gtgagtaaag cccatgcgaa attttcacat aagaaatgca tgcttttgt      900
tttcaacgac atgagttgca tgcttttat cattgcttat atagttgcaa gtttgcaact      960
ccttgatatt ttttttatgt agacactact accaccaaaa acttttggtc tgcttattct    1020
tgtttactat gtaaaaaaaa taaatgaatt gtttatttac tccgatttga tggagtctgg    1080
tttatgaggt tttatagcct ttacagaaaa ttgatagtta caaaatatt tttcaaaat     1140
aaaagggtaa aaccgtcatt tcaagttgtt attgttttgg gggactggat ttgaaatgaa    1200
atatagaacc ggaaaacaag gtgagccgaa gtcgaagcct ttggacccgt ttttatattt    1260
actcctccca ttcccttctc cttcaatcct tccttcctcc tcctcccttc ttcttcttcc    1320
cctctttcat tttccagcca ctacaaactt ttctatctct actttttttc ctctcgattt    1380
caggtacttt ttgagaccct ttgttgtgat tttcgaacac acaccccaat tacgtttgat    1440
ttttgatccc gcatcgattt caattcatcc gttctgagt ttcttttgga tctgggtgtc     1500
ttgagctaat cttttcgatc tgttgtttat cgatttact catgcgtatg ttcattacac     1560
catttgttat ttgtttaatc aaccaaaaga ctcatgtttt tcaaatgtct ttaatataat    1620
ttttctgatt gaatttata atatttacat gattctggat ccagaatatc cttcttcttc    1680
ttccattttg tcctgtattg attttgtcttt gaaaaaggat tgttctttgt atctgtattg   1740
gtgaaaaagg attgttattt gttgataaaa atttgatctt taaacaatgt ttggttttgc    1800
ataaaggtag aagacc                                                    1816

<210> SEQ ID NO 31
<211> LENGTH: 1816
<212> TYPE: DNA
<213> ORGANISM: Artificial Sequence
<220> FEATURE:
<223> OTHER INFORMATION: Synthetic promoter sequence

<400> SEQUENCE: 31
taaatgacat cagatacacg cttgtgaacc atctttaaag tattgatgga ctcttcacta      60
tgaaagctct ctttaaaatt aattttcttt gtacatgtct ctaagcaatg tcaaattaat    120
tagaggtcca aattcaaaaa aatgtcgtat tgaatcattc cattactaaa ttggttcaat    180
gtcagattta aacagcctag gatctacctg cagccaagct agcttgtcag cgtgtcctct    240
ccaaatgaaa tgaacttcct tatatagagg aagggtcttg cgaaggatag tgggattgtg    300
cgtcatccct tacgtcagtg gagatgggga tctcgagtgc gtcatccctt acgtcaggtg    360
cgtcatccct tacgtcaggt gcgtcatccc ttacgtcagg tgcgtcatcc cttacgtcag    420
aagctctagg gataatttag tgagatatga gattctactt tcaacatata ctaatcctaa    480
atctctagca acttttata taagctataa atatcatgaa aatgtatttt aatcgtttca    540
taatttatgc agtcacacta atggaaaaaa ggccaattat tattattttc ttcagactat     600
aaatgaaaac ataattaaa atgcagatta gtttaaaatt ttaataagta agtaaaatgc     660
ttatagcctt atacaaaatc atatttggaa gtttctaaca ttgttgcaat tgttatcac     720
aaatcacagt aatatttgta tactaattag taattacaac tatacacaaa tttaaatggg    780
taatcatata tttgtgtcca gtggattgaa caaatatgct cggcccatgc ggaagtaatg    840
ccaattttgg gtgagtaaag cccatgcgaa attttcacat aagaaatgca tgcttttgt      900
tttcaacgac atgagttgca tgcttttat cattgcttat atagttgcaa gtttgcaact      960
ccttgatatt ttttttatgt agacactact accaccaaaa acttttggtc tgcttattct    1020
```

```
tgtttactat gtaaaaaaaa taaatgaatt gtttatttac tccgatttga tggagtctgg    1080
tttatgaggt tttatagcct ttacagaaaa ttgatagtta caaaaatatt tttcaaaaat    1140
aaaagggtaa aaccgtcatt tcaagttgtt attgttttgg gggactggat ttgaaatgaa    1200
atatagaacc ggaaaacaag gtgagccgaa gtcgaagcct ttggacccgt ttttatattt    1260
actcctccca ttcccttctc cttcaatcct tccttcctcc tcctcccttc ttcttcttcc    1320
cctctttcat tttccagcca ctacaaactt ttctatctct actttttttc ctctcgattt    1380
caggtacttt ttgagaccct tgttgtgat tttcgaacac acaccccaat tacgtttgat     1440
ttttgatccc gcatcgattt caattcatcc gtttctgagt ttcttttgga tctgggtgtc    1500
ttgagctaat cttttcgatc tgttgtttat cgattttact catgcgtatg ttcattacac    1560
catttgttat ttgtttaatc aaccaaaaga ctcatgtttt tcaaatgtct ttaatataat    1620
ttttctgatt gaattttata atatttacat gattctggat ccagaatatc cttcttcttc    1680
ttccattttg tcctgtattg atttgtcttt gaaaaaggat tgttctttgt atctgtattg    1740
gtgaaaaagg attgttattt gttgataaaa atttgatctt taaacaatgt ttggttttgc    1800
ataaaggtag aagacc                                                    1816

<210> SEQ ID NO 32
<211> LENGTH: 1812
<212> TYPE: DNA
<213> ORGANISM: Artificial Sequence
<220> FEATURE:
<223> OTHER INFORMATION: Synthetic promoter sequence

<400> SEQUENCE: 32
taaatgacat cagatacacg cttgtgaacc atctttaaag tattgatgga ctcttcacta      60
tgaaagctct ctttaaaatt aattttcttt gtacatgtct ctaagcaatg tcaaattaat     120
tagaggtcca aattcaaaaa aatgtcgtat tgaatcattc cattactaaa ttggttcaat     180
gtcagattta aacagcctag ggataattta gtgagatatg agattctact ttcaacatat     240
actaatccta aatctctagc aacttttttat ataagctata aatatcatga aaatgtattt    300
taatcgtttc ataatttatg cagtcacact aatggaaaaa aggccaatta ttattatttt     360
cttcagacta taaatgaaaa cataaattaa aatgcagatt agtttaaaat tttaataagt     420
aagtaaaatg cttatagcct tatacaaaat catatttgga agtttctaac attgttgcaa     480
tttgttatca caaatcacag taatatttgt aagcttctga cgtaagggat gacgcacctg     540
acgtaaggga tgacgcacct gacgtaaggg atgacgcacc tgacgtaagg gatgacgcac     600
tcgagatccc catctccact gacgtaaggg atgacgcaca atcccactat ccttcgcaag     660
acccttcctc tatataagga agttcattta atttggagag gacacgctga caagctagct     720
tggctgcagg tagatctact aattagtaat tacaactata cacaaattta aatgggtaat     780
catatatttg tgtccagtgg attgaacaaa tatgctcggc ccatgcggaa gtaatgccaa     840
ttttgggtga gtaaagccca tgcgaaattt tcacataaga aatgcatgct ttttgttttc     900
aacgacatga gttgcatgct ttttatcatt gcttatatag ttgcaagttt gcaactcctt     960
gatatttttt ttatgtagac actactacca ccaaaaactt ttggtctgct tattcttgtt    1020
tactatgtaa aaaaaataaa tgaattgttt atttactccg atttgatgga gtctggttta    1080
tgaggtttta tagcctttac agaaaattga tagttacaaa atatttttc aaaaataaaa     1140 gggtaaaacc gtcatttcaa gttgttattg ttttggggga ctggatttga aatgaaatat    1200
agaaccggaa aacaaggtga gccgaagtcg aagcctttgg acccgttttt atatttactc    1260
```

```
ctcccattcc cttctccttc aatccttcct tcctcctcct cccttcttct tcttccctc      1320 tttcattttc cagccactac aaacttttct atctctactt ttttcctct cgatttcagg       1380 tacttttga gacccttgt tgtgattttc gaacacacac cccaattacg tttgatttt         1440 gatcccgcat cgatttcaat tcatccgttt ctgagtttct tttggatctg ggtgtcttga     1500
gctaatcttt tcgatctgtt gtttatcgat tttactcatg cgtatgttca ttacaccatt     1560
tgttatttgt ttaatcaacc aaaagactca tgttttcaa atgtctttaa tataattttt      1620
ctgattgaat tttataatat ttacatgatt ctggatccag aatatccttc ttcttcttcc    1680
attttgtcct gtattgattt gtctttgaaa aaggattgtt ctttgtatct gtattggtga    1740
aaaaggattg ttatttgttg ataaaaattt gatctttaaa caatgtttgg ttttgcataa    1800
aggtagaaga cc                                                          1812

<210> SEQ ID NO 33
<211> LENGTH: 1812
<212> TYPE: DNA
<213> ORGANISM: Artificial Sequence
<220> FEATURE:
<223> OTHER INFORMATION: Synthetic promoter sequence

<400> SEQUENCE: 33
taaatgacat cagatacacg cttgtgaacc atctttaaag tattgatgga ctcttcacta      60
tgaaagctct ctttaaaatt aattttcttt gtacatgtct ctaagcaatg tcaaattaat    120
tagaggtcca aattcaaaaa aatgtcgtat tgaatcattc cattactaaa ttggttcaat     180
gtcagattta aacagcctag ggataattta gtgagatatg agattctact ttcaacatat    240
actaatccta aatctctagc aacttttat ataagctata aatatcatga aaatgtattt      300
taatcgtttc ataatttatg cagtcacact aatggaaaaa aggccaatta ttattatttt    360
cttcagacta taaatgaaaa cataaattaa aatgcagatt agtttaaaat tttaataagt    420
aagtaaaatg cttatagcct tatacaaaat catatttgga agtttctaac attgttgcaa   480
tttgttatca caaatcacag taatatttgt agatctacct gcagccaagc tagcttgtca    540
gcgtgtcctc tccaaatgaa atgaacttcc ttatatagag gaagggtctt gcgaaggata   600
gtgggattgt gcgtcatccc ttacgtcagt ggagatgggg atctcgagtg cgtcatccct    660
tacgtcaggt gcgtcatccc ttacgtcagg tgcgtcatcc cttacgtcag gtgcgtcatc    720
ccttacgtca gaagcttact aattagtaat tacaactata cacaaattta aatgggtaat    780
catatatttg tgtccagtgg attgaacaaa tatgctcggc ccatgcggaa gtaatgccaa    840
ttttgggtga gtaaagccca tgcgaaattt tcacataaga aatgcatgct ttttgtttc     900 aacgacatga gttgcatgct tttatcatt gcttatatag ttgcaagttt gcaactcctt    960
gatatttttt ttatgtagac actactacca ccaaaaactt tggtctgct tattcttgtt    1020 tactatgtaa aaaaaataaa tgaattgttt atttactccg atttgatgga gtctggttta    1080
tgaggtttta tagcctttac agaaaattga tagttacaaa atatttttc aaaaataaaa    1140 gggtaaaacc gtcatttcaa gttgttattg ttttggggga ctggatttga aatgaaatat    1200
agaaccggaa aacaaggtga gccgaagtcg aagcctttgg acccgttttt atatttactc    1260
ctcccattcc cttctccttc aatccttcct tcctcctcct cccttcttct tcttccctc     1320 tttcattttc cagccactac aaacttttct atctctactt ttttcctct cgatttcagg     1380 tacttttga gacccttgt tgtgattttc gaacacacac cccaattacg tttgatttt      1440
```

-continued

```
gatcccgcat cgatttcaat tcatccgttt ctgagtttct tttggatctg ggtgtcttga    1500
gctaatcttt tcgatctgtt gtttatcgat tttactcatg cgtatgttca ttacaccatt    1560
tgttatttgt ttaatcaacc aaaagactca tgtttttcaa atgtctttaa tataattttt    1620
ctgattgaat tttataatat ttacatgatt ctggatccag aatatccttc ttcttcttcc    1680
attttgtcct gtattgattt gtctttgaaa aggattgtt ctttgtatct gtattggtga     1740
aaaaggattg ttatttgttg ataaaaattt gatctttaaa caatgtttgg ttttgcataa    1800
aggtagaaga cc                                                        1812
```

<210> SEQ ID NO 34
<211> LENGTH: 1840
<212> TYPE: DNA
<213> ORGANISM: Artificial Sequence
<220> FEATURE:
<223> OTHER INFORMATION: Synthetic promoter sequence

<400> SEQUENCE: 34

```
ggccgcctgc aggaagctgt acccccccaag cttaaatgac atcagataca cgcttgtgaa    60
ccatctttaa agtattgatg gactcttcac tatgaaagct ctctttaaaa ttaattttct    120
ttgtacatgt ctctaagcaa tgtcaaatta attagaggtc caaattcaaa aaaatgtcgt    180
attgaatcat tccattacta aattggttca atgtcagatt taaacagcct agggataatt    240
tagtgagata tgagattcta ctttcaacat atactaatcc taaatctcta gcaactttt    300 atataagcta taaatatcat gaaaatgtat tttaatcgtt tcataattta tgcagtcaca    360
ctaatggaaa aaaggccaat tattattatt ttcttcagac tataaatgaa aacataaatt    420
aaaatgcaga ttagtttaaa attttaataa gtaagtaaaa tgcttatagc cttatacaaa    480
atcatatttg gaagtttcta acattgttgc aatttgttat cacaaatcac agtaatattt    540
gtatactaat tagtaattac aactatacac aaatttaaat gggtaatcat atatttgtgt    600
ccagtggatt gaacaaatat gctcggccca tgcggaagta atgccaattt tgggtgagta    660
aagcccatgc gaattttca cataagaaaa gcttctgacg taaggatga cgcacctgac     720 gtaagggatg acgcacctga cgtaagggat gacgcacctg acgtaaggga tgacgcactc    780
gagatcccca tctccactga cgtaagggat gacgcacaat cccactatcc ttcgcaagac    840
ccttcctcta taaggaag ttcatttcat ttggagagga cacgctgaca agctagcttg     900
gctgcaggta gatctgcttt ttgttttcaa cgacatgagt tgcatgcttt ttatcattgc    960
ttatatagtt gcaagtttgc aactccttga tatttttttt atgtagacac tactaccacc   1020 aaaaacttt ggtctgctta ttcttgttta ctatgtaaaa aaataaatg aattgtttat     1080 ttactccgat ttgatggagt ctggtttatg aggttttata gccttacag aaaattgata    1140 gttacaaaaa tattttcaa aaataaaagg gtaaaaccgt catttcaagt tgttattgtt    1200
ttgggggact ggatttgaaa tgaaatatag aaccggaaaa caaggtgagc cgaagtcgaa    1260
gcctttggac ccgttttttat atttactcct cccattccct tctccttcaa tccttccttc    1320
ctcctcctcc cttcttcttc tccccctctt tcatttccca gccactacaa acttttctat    1380
ctctactttt tttcctctcg atttcaggta cttttgaga ccctttgttg tgattttcga     1440
acacacaccc caattacgtt tgattttga tcccgcatcg atttcaattc atccgtttct    1500
gagtttcttt tggatctggg tgtcttgagc taatcttttc gatctgttgt ttatcgattt    1560
tactcatgcg tatgttcatt acaccatttg ttatttgttt aatcaaccaa aagactcatg    1620
tttttcaaat gtctttaata taattttct gattgaattt tataatattt acatgattct     1680
```

```
ggatccagaa tatccttctt cttcttccat tttgtcctgt attgatttgt ctttgaaaaa    1740
ggattgttct ttgtatctgt attggtgaaa aaggattgtt atttgttgat aaaaatttga    1800
tctttaaaca atgtttggtt ttgcataaag gtagaagacc                          1840

<210> SEQ ID NO 35
<211> LENGTH: 1848
<212> TYPE: DNA
<213> ORGANISM: Artificial Sequence
<220> FEATURE:
<223> OTHER INFORMATION: Synthetic promoter sequence

<400> SEQUENCE: 35
ggccgcctgc aggaagctgt acccccccaag cttaaatgac atcagataca cgcttgtgaa     60
ccatctttaa agtattgatg gactcttcac tatgaaagct ctctttaaaa ttaattttct    120
ttgtacatgt ctctaagcaa tgtcaaatta attagaggtc caaattcaaa aaaatgtcgt    180
attgaatcat tccattacta aattggttca atgtcagatt taaacagcct agggataatt    240
tagtgagata tgagattcta ctttcaacat atactaatcc taaatctcta gcaacttttt    300
atataagcta taaatatcat gaaaatgtat tttaatcgtt tcataattta tgcagtcaca    360
ctaatggaaa aaaggccaat tattattatt ttcttcagac tataaatgaa acataaaatt    420
aaaatgcaga ttagtttaaa attttaataa gtaagtaaaa tgcttatagc cttatacaaa    480
atcatatttg gaagtttcta acattgttgc aatttgttat cacaaatcac agtaatattt    540
gtatactaat tagtaattac aactatacac aaatttaaat gggtaatcat atatttgtgt    600
ccagtggatt gaacaaatat gctcggccca tgcggaagta atgccaattt tgggtgagta    660
aagcccatgc gaaattttca cataagaaat gcatgctttt tgttttcaac gacatgagtt    720
gcatgctttt tatcattgct tatatagttg caagtttgca actccttgat atttttttta    780
tgtagacact actaccacca aaaacttttg gtctgcttat tcttgtttac tatgtaaaaa    840
aaataaatga attgtttatt tactccgatt tgatggagtc tggtttatga ggttttatag    900
cctttacaga aaattgatag ttacaaaaat atttttcaaa aataaaaggg taaaaccgtc    960
atttcaagtt gttattgttt tggggactg gatttgaaat gaagcttctg acgtaaggga   1020
tgacgcacct gacgtaaggg atgacgcacc tgacgtaagg gatgacgcac ctgacgtaag   1080
ggatgacgca ctcgagatcc ccatctccac tgacgtaagg gatgacgcac aatcccacta   1140
tccttcgcaa gacccttcct ctatataagg aagttcattt catttggaga ggacacgctg   1200
acaagctagc ttggctgcag gtagatcatg aaatatagaa ccggaaaaca aggtgagccg   1260
aagtcgaagc cttggacccc gttttttatat ttactcctcc cattcccttc ccttcaatc   1320 cttccttcct cctcctccct tcttcttctt cccctctttc attttccagc cactacaaac   1380 tttttctatct ctactttttt tcctctcgat ttcaggtact ttttgagacc ctttgttgtg   1440
attttcgaac acacacccca attacgtttg attttttgatc ccgcatcgat ttcaattcat   1500
ccgtttctga gttcttttg gatctgggtg tcttgagcta atcttttcga tctgttgttt   1560
atcgatttta ctcatgcgta tgttcattac accatttgtt atttgtttaa tcaaccaaaa   1620
gactcatgtt tttcaaatgt ctttaatata attttttctga ttgaattta taatatttac   1680 atgattctgg atccagaata tccttcttct tcttccattt tgtcctgtat tgatttgtct   1740
ttgaaaaagg attgttcttt gtatctgtat tggtgaaaaa ggattgttat ttgttgataa   1800
aaatttgatc tttaaacaat gtttggtttt gcataaaggt agaagacc                1848
```